(12) United States Patent
Liu et al.

(10) Patent No.: US 11,214,624 B2
(45) Date of Patent: Jan. 4, 2022

(54) METHOD TO PREVENT CANCER METASTASIS AND INHIBIT INFLAMMATION BY INHIBITION OF P68 INTERACTION WITH CALMODULIN

(71) Applicant: Proda Biotech LLC, Marietta, GA (US)

(72) Inventors: Zhi-Ren Liu, Marietta, GA (US); Haizhen Wang, Chestnuts, MA (US)

(73) Assignee: Proda Biotech LLC, Marietta, GA (US)

( * ) Notice: Subject to any disclaimer, the term of this patent is extended or adjusted under 35 U.S.C. 154(b) by 0 days.

(21) Appl. No.: 14/385,061

(22) PCT Filed: Mar. 13, 2013

(86) PCT No.: PCT/US2013/030956
§ 371 (c)(1),
(2) Date: Sep. 12, 2014

(87) PCT Pub. No.: WO2013/138484
PCT Pub. Date: Sep. 19, 2013

(65) Prior Publication Data
US 2015/0037342 A1  Feb. 5, 2015

Related U.S. Application Data

(60) Provisional application No. 61/610,853, filed on Mar. 14, 2012.

(51) Int. Cl.
| | |
|---|---|
| *C07K 16/40* | (2006.01) |
| *C12N 9/14* | (2006.01) |
| *C07K 14/47* | (2006.01) |
| *A61K 38/46* | (2006.01) |
| *G01N 33/50* | (2006.01) |
| *G01N 33/573* | (2006.01) |
| *A61K 38/00* | (2006.01) |

(52) U.S. Cl.
CPC .............. *C07K 16/40* (2013.01); *A61K 38/46* (2013.01); *C07K 14/4728* (2013.01); *C12N 9/14* (2013.01); *G01N 33/5011* (2013.01); *G01N 33/573* (2013.01); *A61K 38/00* (2013.01); *C07K 2317/76* (2013.01); *C07K 2319/10* (2013.01); *C12Y 306/04013* (2013.01); *G01N 2333/914* (2013.01); *G01N 2500/02* (2013.01); *Y02A 50/30* (2018.01)

(58) Field of Classification Search
CPC ...................................... A61K 16/40
USPC ...................................... 424/139.1
See application file for complete search history.

(56) References Cited

U.S. PATENT DOCUMENTS 5,585,475 A * 12/1996 Jamieson ................ C07K 7/08
530/324

OTHER PUBLICATIONS

Buelt et al (JBC, 1994, 269(47): 29367-29370).*
Burgess et al. (J. Cell Biol. 111:2129-2138, 1990).*
Lazar et al. ( Mol. Cell Biol. 8:1247-1252, 1998).*
Smith et al (Molecular Brain Research, 1998, 62: 12-24).*
Kleerekoper et al (JBC, 2009, 284(12): 7455-7464).*

* cited by examiner

*Primary Examiner* — Sean E Aeder
(74) *Attorney, Agent, or Firm* — Greenberg Traurig LLP

(57) ABSTRACT

Compositions and methods for inhibiting cancer cell metastasis and inflammation are disclosed. The methods generally involve administering to a subject a composition containing an agent that selectively inhibits the binding of p68 RNA helicase to calmodulin (CaM) in the cells.

7 Claims, 12 Drawing Sheets
Specification includes a Sequence Listing.

SEQUENCE LISTING

```
<160> NUMBER OF SEQ ID NOS: 8

<210> SEQ ID NO 1
<211> LENGTH: 614
<212> TYPE: PRT
<213> ORGANISM: Artificial Sequence
<220> FEATURE:
<223> OTHER INFORMATION: Human fragments or modifications thereto

<400> SEQUENCE: 1

Met Ser Gly Tyr Ser Ser Asp Arg Asp Arg Gly Arg Asp Arg Gly Phe
1               5                   10                  15

Gly Ala Pro Arg Phe Gly Gly Ser Arg Ala Gly Pro Leu Ser Gly Lys
            20                  25                  30

Lys Phe Gly Asn Pro Gly Glu Lys Leu Val Lys Lys Lys Trp Asn Leu
        35                  40                  45

Asp Glu Leu Pro Lys Phe Glu Lys Asn Phe Tyr Gln Glu His Pro Asp
    50                  55                  60

Leu Ala Arg Arg Thr Ala Gln Glu Val Glu Thr Tyr Arg Arg Ser Lys
65                  70                  75                  80

Glu Ile Thr Val Arg Gly His Asn Cys Pro Lys Pro Val Leu Asn Phe
                85                  90                  95

Tyr Glu Ala Asn Phe Pro Ala Asn Val Met Asp Val Ile Ala Arg Gln
            100                 105                 110

Asn Phe Thr Glu Pro Thr Ala Ile Gln Ala Gln Gly Trp Pro Val Ala
        115                 120                 125
```

```
Leu Ser Gly Leu Asp Met Val Gly Val Ala Gln Thr Gly Ser Gly Lys
130                 135                 140

Thr Leu Ser Tyr Leu Leu Pro Ala Ile Val His Ile Asn His Gln Pro
145                 150                 155                 160

Phe Leu Glu Arg Gly Asp Gly Pro Ile Cys Leu Val Leu Ala Pro Thr
                165                 170                 175

Arg Glu Leu Ala Gln Gln Val Gln Gln Val Ala Ala Glu Tyr Cys Arg
                180                 185                 190

Ala Cys Arg Leu Lys Ser Thr Cys Ile Tyr Gly Gly Ala Pro Lys Gly
                195                 200                 205

Pro Gln Ile Arg Asp Leu Glu Arg Gly Val Glu Ile Cys Ile Ala Thr
210                 215                 220

Pro Gly Arg Leu Ile Asp Phe Leu Glu Cys Gly Lys Thr Asn Leu Arg
225                 230                 235                 240

Arg Thr Thr Tyr Leu Val Leu Asp Glu Ala Asp Arg Met Leu Asp Met
                245                 250                 255

Gly Phe Glu Pro Gln Ile Arg Lys Ile Val Asp Gln Ile Arg Pro Asp
                260                 265                 270

Arg Gln Thr Leu Met Trp Ser Ala Thr Trp Pro Lys Glu Val Arg Gln
                275                 280                 285

Leu Ala Glu Asp Phe Leu Lys Asp Tyr Ile His Ile Asn Ile Gly Ala
290                 295                 300

Leu Glu Leu Ser Ala Asn His Asn Ile Leu Gln Ile Val Asp Val Cys
305                 310                 315                 320

His Asp Val Glu Lys Asp Glu Lys Leu Ile Arg Leu Met Glu Glu Ile
                325                 330                 335

Met Ser Glu Lys Glu Asn Lys Thr Ile Val Phe Val Glu Thr Lys Arg
                340                 345                 350

Arg Cys Asp Glu Leu Thr Arg Lys Met Arg Arg Asp Gly Trp Pro Ala
                355                 360                 365

Met Gly Ile His Gly Asp Lys Ser Gln Gln Glu Arg Asp Trp Val Leu
370                 375                 380

Asn Glu Phe Lys His Gly Lys Ala Pro Ile Leu Ile Ala Thr Asp Val
385                 390                 395                 400

Ala Ser Arg Gly Leu Asp Val Glu Asp Val Lys Phe Val Ile Asn Tyr
                405                 410                 415

Asp Tyr Pro Asn Ser Ser Glu Asp Tyr Ile His Arg Ile Gly Arg Thr
                420                 425                 430

Ala Arg Ser Thr Lys Thr Gly Thr Ala Tyr Thr Phe Phe Thr Pro Asn
                435                 440                 445

Asn Ile Lys Gln Val Ser Asp Leu Ile Ser Val Leu Arg Glu Ala Asn
450                 455                 460

Gln Ala Ile Asn Pro Lys Leu Leu Gln Leu Val Glu Asp Arg Gly Ser
465                 470                 475                 480

Gly Arg Ser Arg Gly Arg Gly Met Lys Asp Asp Arg Arg Asp Arg
                485                 490                 495

Tyr Ser Ala Gly Lys Arg Gly Phe Asn Thr Phe Arg Asp Arg Glu
                500                 505                 510

Asn Tyr Asp Arg Gly Tyr Ser Ser Leu Leu Lys Arg Asp Phe Gly Ala
                515                 520                 525

Lys Thr Gln Asn Gly Val Tyr Ser Ala Ala Asn Tyr Thr Asn Gly Ser
530                 535                 540
```

-continued

```
Phe Gly Ser Asn Phe Val Ser Ala Gly Ile Gln Thr Ser Phe Arg Thr
545                 550                 555                 560

Gly Asn Pro Thr Gly Thr Tyr Gln Asn Gly Tyr Asp Ser Thr Gln Gln
            565                 570                 575

Tyr Gly Ser Asn Val Pro Asn Met His Asn Gly Met Asn Gln Gln Ala
        580                 585                 590

Tyr Ala Tyr Pro Ala Thr Ala Ala Pro Met Ile Gly Tyr Pro Met
    595                 600                 605

Pro Thr Gly Tyr Ser Gln
    610

<210> SEQ ID NO 2
<211> LENGTH: 19
<212> TYPE: PRT
<213> ORGANISM: Artificial Sequence
<220> FEATURE:
<223> OTHER INFORMATION: Human fragments or modifications thereto

<400> SEQUENCE: 2

Met His Asn Gly Met Asn Gln Gln Ala Tyr Ala Tyr Pro Ala Thr Ala
1               5                   10                  15

Ala Ala Pro

<210> SEQ ID NO 3
<211> LENGTH: 20
<212> TYPE: PRT
<213> ORGANISM: Artificial Sequence
<220> FEATURE:
<223> OTHER INFORMATION: Human fragments or modifications thereto

<400> SEQUENCE: 3

Met His Asn Gly Met Asn Gln Gln Ala Pro Tyr Ala Tyr Pro Ala Thr
1               5                   10                  15

Ala Ala Ala Pro
            20

<210> SEQ ID NO 4
<211> LENGTH: 40
<212> TYPE: PRT
<213> ORGANISM: Artificial Sequence
<220> FEATURE:
<223> OTHER INFORMATION: Human fragments or modifications thereto

<400> SEQUENCE: 4

Met His Asn Gly Met Asn Gln Gln Ala Pro Tyr Ala Tyr Pro Ala Thr
1               5                   10                  15

Ala Ala Ala Pro Phe Val Ser Ala Gly Ile Gln Thr Ser Phe Arg Thr
            20                  25                  30

Gly Asn Pro Thr Gly Ala Tyr Gly
            35                  40

<210> SEQ ID NO 5
<211> LENGTH: 20
<212> TYPE: PRT
<213> ORGANISM: Artificial Sequence
<220> FEATURE:
<223> OTHER INFORMATION: Human fragments or modifications thereto

<400> SEQUENCE: 5

Phe Val Ser Ala Gly Ile Gln Thr Ser Phe Arg Thr Gly Asn Pro Thr
1               5                   10                  15
```

```
Gly Ala Tyr Gly
        20

<210> SEQ ID NO 6
<211> LENGTH: 20
<212> TYPE: PRT
<213> ORGANISM: Artificial Sequence
<220> FEATURE:
<223> OTHER INFORMATION: Human fragments or modifications thereto

<400> SEQUENCE: 6

Phe Ala Ser Gly Gln Ile Asn Thr Phe Val Ser Arg Gly Thr Pro Gly
1               5                   10                  15

Tyr Ala Thr Gly
        20

<210> SEQ ID NO 7
<211> LENGTH: 17
<212> TYPE: PRT
<213> ORGANISM: Artificial Sequence
<220> FEATURE:
<223> OTHER INFORMATION: Human fragments or modifications thereto

<400> SEQUENCE: 7

Phe Val Ser Ala Gly Ile Gln Thr Ser Phe Arg Thr Gly Asn Pro Thr
1               5                   10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: Human fragments or modifications thereto

<400> SEQUENCE: 8

Gly Arg Lys Lys Arg Arg Gln Arg Arg Gly
1               5                   10
```

METHOD TO PREVENT CANCER METASTASIS AND INHIBIT INFLAMMATION BY INHIBITION OF P68 INTERACTION WITH CALMODULIN

PRIOR RELATED APPLICATION DATA

This application claims priority to U.S. Provisional Patent Application Ser. No. 61/610,853, filed Mar. 14, 2012, which is incorporated by reference in its entirety.

STATEMENT REGARDING FEDERALLY SPONSORED RESEARCH OR DEVELOPMENT

This invention was made with Government Support under Agreement CA118113 by the National Institutes of Health. The Government has certain rights in the invention.

FIELD OF THE INVENTION

The invention is generally related cell migration, more particularly to compositions and methods for inhibiting cancer cell metastasis and inflammation.

BACKGROUND

While there have been tremendous advances in cancer research and treatment, cancer is the second leading cause of death in the U.S. About 90% of these deaths are due to metastasis, which is the ability of cancer cells to migrate from their tissue of origin and colonize elsewhere in the body.

SUMMARY

Compositions and methods for inhibiting cell migration are disclosed. Aberrant cell migration is involved in, for example, metastasis and inflammation. Therefore, compositions and methods for inhibiting cancer cell metastasis or inflammation are disclosed. The methods generally involve administering to a subject in need thereof a composition containing an agent that selectively inhibits the binding of p68 RNA helicase to calmodulin (CaM) in the cancer cells.

In some embodiments, the agent is a peptide containing the IQ motif of human p68, or a conservative variant thereof that binds human CaM. The human p68 IQ motif has the amino acid sequence FVSAGIQTSF RTGNPTGTYQ (SEQ ID NO:8). However, the agent can also be peptide with the amino acid sequence FVSAGIQTSF RTGNPTG (SEQ ID NO:7) or FVSAGIQTSFRTGNPTGAYG (SEQ ID NO:4).

In some embodiments, peptides for use in the disclosed methods are of a size and charge for effective penetration of cancer cells. In some embodiments, the peptide is 6 to 30 amino acids in length. In some embodiments, the disclosed peptide further contains a cell penetration (internalization) sequence.

In other embodiments, the agent is an antibody that selectively binds the IQ motif of p68 RNA helicase in the cancer cells.

Methods for identifying agents for inhibiting cancer metastasis are also disclosed. Such methods generally involve contacting a candidate agent to a sample containing a p68 peptide and a CaM peptide under conditions suitable for the binding of the p68 peptide to the CaM peptide, and detecting the binding of the p68 peptide to the CaM peptide. In these methods, a decrease in p68/CaM binding compared to a control sample is an indication of an agent that inhibits cancer metastasis. In one example, the p68 peptide contains at least the IQ motif of human p68 RNA helicase, or a conservative variant thereof that binds human CaM, and the CaM peptide contains at least the p68-binding region of human CaM, or a conservative variant thereof that binds p68.

Pharmaceutical compositions for use in treating cancer and inhibiting cancer metastasis are also disclosed. The pharmaceutical compositions can have a peptide that selectively inhibits the binding of p68 RNA helicase to CaM and a pharmaceutically acceptable carrier. In some embodiments, the pharmaceutical composition is in a unit dose for inhibiting metastatis of a cancer in a subject. In examples, a dose of between about and 1 and 2 mg/kg of the binding agents were effective. In some embodiments, the pharmaceutical composition further contains an anti-neoplastic agent.

An isolated peptide containing the IQ motif of human p68, or a conservative variant thereof that binds human CaM, and a cell penetration sequence is also disclosed.

DETAILED DESCRIPTION

I. Definitions

Figure 1A:
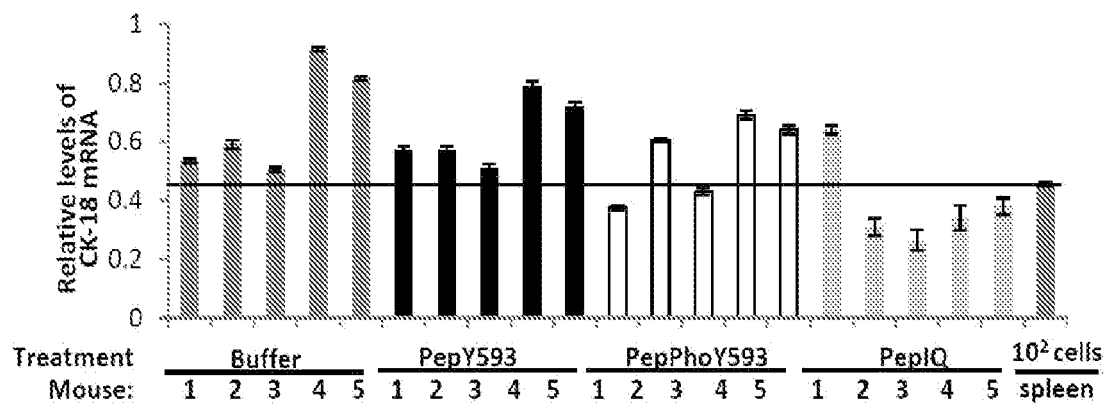
FIG. 1A is graph showing human cytokarotine-18 (CK-18) mRNA levels (quantitative RT-PCR, relative to β-actin) 1) from the spleen extracts of mice with xenograft of SW620 tumors that were treated with buffer (columns 1-5), a p68 peptide fragment spanning aa 584-602 ("PepY593," SEQ ID NO:2) (columns 6-10), phosphorylated PepY593 peptide ("PepPhoY593," SEQ ID NO:3) (columns 11-15), or a p68 peptide fragment spanning aa 549-568 ("PepIQ," SEQ ID NO:4) (columns 16-20), each fused with the TAT cell permeable sequence (SEQ ID NO:6) at the N-terminus; or 2) from spleen harvested from mice without tumor implantation but with direct injection of 100 SW620 cells ($10^2$ cells/spleen).

The term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "anti-cancer" or "antineoplastic" refers to a composition, such as a drug or biologic, that can inhibit or prevent cancer growth, invasion, and/or metastasis.

The term "individual," "host," "subject," and "patient" are used interchangeably to refer to any individual who is the target of administration or treatment. The subject can be a vertebrate, for example, a mammal. Thus, the subject can be a human or veterinary patient.

The term "therapeutically effective" means that the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "peptide," "protein," and "polypeptide" are used interchangeably to refer to a natural or synthetic molecule comprising two or more amino acids linked by the carboxyl group of one amino acid to the alpha amino group of another.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "small molecule" refers to a molecule, such as an organic or organometallic compound, with a molecular weight of less than 2,000 Daltons, or less than 1,500 Daltons, or less than 1,000 Daltons. The small molecule can be a hydrophilic, hydrophobic, or amphiphilic compound.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "variant" refers to a peptide (e.g., the IQ motif) having one or more modifications relative to wild-type (such as substitutions, insertions, deletions, and/or truncations of one or more amino acid residues, respectively), and biologically active fragments thereof. In some embodiments, a variant peptide is a peptide that is structurally/sequence related to a reference peptide comprising in SEQ ID NOs:1 through 8 or a fragment thereof having binding activity to Ca-Calmodulin, but has one or more amino acid substitutions in relation to the reference peptide. Such variant may be a cyclized variation of such the wild-type peptide and may include natural and unnatural amino acids (e.g., analogue amino acids).

The term "specifically binds" refers to a binding reaction which is determinative of the presence of the antigen or receptor in a heterogeneous population of proteins and other biologics. Generally, a first molecule (e.g., antibody) that "specifically binds" a second molecule (e.g., antigen) has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

II. Compositions

Agents that inhibit the interaction of p68 RNA helicase and calmodulin (CaM) in a cell are disclosed for used in the disclosed compositions and methods. In some embodiments, the agent binds p68 and blocks the binding of p68 to CaM. In other embodiments, the agent binds CaM and blocks the binding of p68 to CaM.

A. Peptides and Peptidomimetics

In some embodiments, the agent inhibiting the interaction of p68 and CaM is an isolated peptide or peptidomimetic. Any disclosure of a peptide is understood to also include the disclosure of a peptidomimetic of that peptide.

In other embodiments, the peptide is a fragment of p68 RNA helicase that selectively binds CaM, or a conservative variant thereof. Such segments can be referred to as "CaM-binding segments." In some embodiments, this p68 peptide contains the IQ motif of p68, or a conservative variant thereof that selectively binds CaM.

Generally, a first molecule, such as the disclosed peptides, that selectively binds a second molecule has a binding affinity greater than about $10^5$ (e.g., $10^6$, $10^7$, $10^8$, $10^9$, $10^{10}$, $10^{11}$, and $10^{12}$ or more) moles/liter for that second molecule.

The disclosed peptides can have a variety of lengths and structures as described herein. In some aspects, each peptide is from about 4 to about 50 amino acids in length, including about 4, 5, 6, 7, 8, 9, 10, 11, 12, 13, 14, 15, 16, 17, 18, 19, 20, 25, 30, 35, 40, 45, or 50 amino acids. The peptide can be less than about 100 amino acid residues, including less than about 100, 95, 90, 85, 80, 75, 70, 65, 60, 55, 50, 45, 40, 35, 30, 25, 20 amino acid residues. The peptide can be more than about 8 amino acid residues in length, including more than about 8, 9, 10, 11, 12, 13, 14, 15, 16, 17, 18, 19, 20, 25, 30, 35, 40, 45, or 50 amino acid residues.

In some embodiments, the CaM-binding peptide has the amino acid sequence FVSAGIQTSF RTGNPTGTYQ (SEQ ID NO:8), FVSAGIQTSF RTGNPTG (SEQ ID NO:7), FVSAGIQTSFRTGNPTGAYG (SEQ ID NO:4). In other embodiments, the CaM-binding peptide is a conservative variant of this sequence that binds CaM. In some cases, the CaM-binding peptide contains 10, 11, 12, 13, 14, 15, 16, 17, 18, 19, or 20 of the amino acids in SEQ ID NO:4 that binds CaM. For example, the SEQ ID NO:4 contains a T to A substitution at position 18 and a Q to G substitution at position 20 compared to aa 566 and 568 of human p68 (Accession No. NP_004387).

In order to increase efficiency, the disclosed isolated polypeptide can be polymeric. For example, Multiple Antigen Peptide System (MAPS) is based on a small immunologically inert core molecule of radially branching lysine dendrites onto which a number of peptide antigens are anchored. The result is a large macromolecule which has a high molar ratio of peptide antigen to core molecule and does not require further conjugation to a carrier protein.

Thus, the isolated polypeptide can have two or more CaM-binding segments, including 2, 3, 4, 5, 6, 7, 8, 9, 10, 11, 12, 13, 14, 15 or more segments. In some aspects, the isolated polypeptide is unbranched, wherein two or more segments are on the same linear polypeptide. In other aspects, the isolated polypeptide comprises two or more amino acid branches, including 2, 3, 4, 5, 6, 7, 8, 9, 10, 11, 12, 13, 14, 15 or more amino acid branches. Thus, the isolated polypeptide can have a peptidyl core of 2, 3, 4, 5, 6, 7, 8, 9, 10 or more branched lysine residues, wherein two or more of the CaM-binding segments are linked to two or more branched lysine residues. In addition, each of the branches can be monomeric or polymeric.

In some aspects, at least one CaM-binding segment is less than about 0 to about 20 amino acids from the amino terminus of the polypeptide, including about 0, 1, 2, 3, 4, 5, 6, 7, 8, 9, 10, 11, 12, 13, 14, 15, 16, 17, 18, 19, or 20 amino acids from the amino terminus.

The disclosed peptides can be artificial sequences and can be synthesized in vitro and/or recombinantly. The disclosed peptides can be isolated from naturally occurring proteins. The peptides that have at least two contiguous sequences that are not contiguous in a naturally occurring protein.

1. Cell Penetrating Peptide

The disclosed composition can be linked to a cell penetrating peptide (a.k.a. protein transduction domains) to effectively enter the cell.

Cell-penetrating peptides are short peptides that facilitate cellular uptake of various molecular cargo, e.g., other peptides. The "cargo" is associated with the cell penetrating peptide either through chemical linkage via covalent bonds or through non-covalent interactions. Cell penetrating peptides typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively.

Cell-Penetrating peptides are of different sizes, amino acid sequences, and charges but all cell penetrating peptides have one distinct characteristic, which is the ability to translocate the plasma membrane and facilitate the delivery of various molecular cargoes to the cytoplasm or an organelle. The mechanism of translocation may involve direct penetration in the membrane, endocytosis-mediated entry, or translocation through the formation of a transitory structure.

Non-limiting examples of cell penetrating peptides include polyarginine, Antennapedia sequences, HIV-1 Tat and related peptides, SynB1, SynB3, PTD-4, PTD-5, penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

2. Fusion Proteins

In some embodiments, the disclosed peptides are fusion proteins. Fusion proteins, also know as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography). Chimeric proteins can also be manufactured with toxins or anti-bodies attached to them in order to study disease development.

Alternatively, internal ribosome entry sites (IRES) elements can be used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

B. Antibodies

In some embodiments, the agent inhibiting the interaction of p68 and CaM is an antibody. Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies. Therefore, the disclosed antibodies contain at least the CDRs necessary to bind p68 or CaM and inhibiting the interaction of p68 and CaM.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific for the CaM-binding domain of p68. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

Humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

Single-Chain Antibodies

A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

Monovalent Antibodies

In vitro methods are also suitable for preparing monovalent antibodies. Digestion of antibodies to produce fragments thereof, particularly, Fab fragments, can be accomplished using routine techniques. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

Hybrid Antibodies

The disclosed antibody may be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

C. Pharmaceutical Compositions

Pharmaceutical compositions that contain therapeutically effective amounts of one or more of the disclosed agents that inhibit the binding of p68 to CaM and a pharmaceutically acceptable carrier are disclosed. Pharmaceutical carriers suitable for administration of the compounds provided herein include any such carriers known to those skilled in the art to be suitable for the particular mode of administration.

The pharmaceutical compounds may be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers.

In some embodiments, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active agent is included in the pharmaceutically acceptable carrier in an amount sufficient to exert a therapeutically useful effect in the absence of undesirable side effects on the patient treated. The therapeutically effective concentration may be determined empirically by testing the compounds in in vitro, ex vivo, and in vivo systems, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In instances in which the compositions exhibit insufficient solubility, methods for solubilizing compounds may be used. Such methods include, but are not limited to, using cosolvents, such as dimethylsulfoxide (DMSO), using surfactants, such as TWEEN®, or dissolution in aqueous sodium bicarbonate.

Liquid pharmaceutically administrable compositions can, for example, be prepared by dissolving, dispersing, or otherwise mixing an active composition as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Dosage forms or compositions containing active ingredient in the range of 0.005% to 100% with the balance made up from non-toxic carrier may be prepared. The contemplated compositions may contain 0.001%-100% active ingredient, or in one embodiment 0.1-95%.

D. Combinations

Numerous anti-cancer (antineoplastic) drugs are available for combination with the present method and compositions. Antineoplastic drugs include Acivicin, Aclarubicin, Acodazole Hydrochloride, AcrQnine, Adozelesin, Aldesleukin, Altretamine, Ambomycin, Ametantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Caracemide, Carbetimer, Carboplatin, Carmustine, Carubicin Hydrochloride, Carzelesin, Cedefingol, Chlorambucil, Cirolemycin, Cisplatin, Cladribine, Crisnatol Mesylate, Cyclophosphamide, Cytarabine, Dacarbazine, Dactinomycin, Daunorubicin Hydrochloride, Decitabine, Dexormaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflomithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, Flurocitabine, Fosquidone, Fostriecin Sodium, Gemcitabine, Gemcitabine Hydrochloride, Gold Au 198, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-Ib, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rogletimide, Safmgol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Tiazofurin, Tirapazamine, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine Sulfate, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride.

III. Methods

A. Treating Cancer

Methods of treating cancer in a subject are disclosed that involve administering to a subject in need thereof a composition that inhibits the interaction of p68 with CaM. In particular, the disclosed method inhibits cancer metastasis.

The cancer of the disclosed methods can be any cell in a subject undergoing unregulated growth, invasion, and/or metastasis. In some aspects, the cancer can be any neoplasm or tumor for which radiotherapy is currently used. Alternatively, the cancer can be a neoplasm or tumor that is not sufficiently sensitive to radiotherapy using standard methods.

The cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

A. Treating Inflammation

Methods of inhibiting inflammation and/or treating an inflammatory disease in a subject are disclosed. These methods involve administering to a subject in need thereof a composition that inhibits the interaction of p68 with CaM.

The inflammatory disease can be an allergic disorder, asthma, childhood wheezing, chronic obstructive pulmonary disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. rhinitis, nasal polyposis, and otitis media), eye diseases (e.g. conjunctivitis and giant papillary conjunctivitis), skin diseases (e.g. psoriasis, dermatitis, and eczema), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Loffler's syndrome and Kawasaki disease), cardiovascular diseases (e.g. atherosclerosis), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain, toxic oil syndrome, endotoxin chock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), sickle cell anemia, hypereosinofilic syndrome, and malignancies (e.g. Hodgkins lymphoma, leukemia (e.g. eosinophil leukemia and chronic myelogenous leukemia), mastocytos, polycytemi vera, and ovarian carcinoma). In particular, compounds of the invention may be useful in treating allergic disorders, asthma, rhinitis, conjunctivitis, COPD, cystic fibrosis, dermatitis, urticaria, eosinophilic gastrointestinal diseases, inflammatory bowel disease, rheumatoid arthritis, osteoarthritis and pain.

B. Administration

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for cancer. Thus, the method can further involve identifying a subject at risk for cancer prior to administration of the herein disclosed compostions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

C. Screening Method

Methods of identifying an agent that can be used to treat cancer or inflammation are disclosed. The method can involve providing a sample containing p68 peptides and CaM peptides under conditions that allow the binding of the p68 and CaM peptides, contacting the sample with a candidate agent, detecting the level of p68/CaM binding, and comparing the binding level to a control. In this method, a decrease in p68/CaM binding compared to the control can identify an agent that can be used to treat cancer.

The binding of p68 and CaM can be detected using routine methods, such as immunodetection methods, that do not disturb protein binding. The methods can be cell-based or cell-free assays. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

The binding of p68 and CaM can be detected using fluorescence activated cell sorting (FACS). For example, disclosed are cell lines transfected with p68 and CaM fused to fluorescent proteins. These cell lines can facilitate high-throughput screens for biologically expressed and small molecule binding to p68 and CaMin their physiological forms.

In general, candidate agents can be identified from large libraries of natural products or synthetic (or semi-synthetic) extracts or chemical libraries. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from purveyors of chemical libraries including but not limited to ChemBridge Corporation (San Diego, Calif.), ChemDiv (San Diego, Calif.), Life Chemicals (Orange, Conn.), and Maybridge (Cornwall, UK).

Alternatively, libraries of natural compounds in the form of bacterial, fungal, plant, and animal extracts are commercially available from a number of sources, including O2H (Cambridge, UK), MerLion Pharmaceuticals Pte Ltd (Singapore Science Park II, Singapore 117528), and Galapagos NV (Mechelen, Belgium).

In addition, natural and synthetically produced libraries can be produced, e.g., by standard extraction and fractionation methods or by standard synthetic methods in combination with solid phase organic synthesis, micro-wave synthesis and other rapid throughput methods amenable to making large numbers of compounds for screening purposes. Furthermore, if desired, any library or compound, including sample format and dissolution is readily modified and adjusted using standard chemical, physical, or biochemical methods.

When a crude extract is found to have a desired activity, further fractionation of the positive lead extract is necessary to isolate chemical constituents responsible for the observed effect. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified. Compounds identified as being of therapeutic value may be subsequently analyzed using in vitro cell based models and animal models for diseases or conditions, such as those disclosed herein.

Candidate agents encompass numerous chemical classes, but are most often organic molecules, e.g., small organic compounds having a molecular weight of more than 100 and less than about 2,500 Daltons. Candidate agents can include functional groups necessary for structural interaction with proteins, particularly hydrogen bonding, and typically include at least an amine, carbonyl, hydroxyl or carboxyl group, for example, at least two of the functional chemical groups. The candidate agents often contain cyclical carbon or heterocyclic structures and/or aromatic or polyaromatic structures substituted with one or more of the above functional groups.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

EXAMPLES

Example 1

A Peptide Fragment of p68 (aa 549-568) Inhibits Cancer Metastasis

Materials and Methods
Reagents, Cell Lines, Antibodies, and Clones:
The HA peptide was synthesized by AnaSpec. HA-tagged p68 encoding DNA sequence was cloned into the pHM6 vector. Cell line SW480/SW620 was purchased from ATCC and cultured by following the vendor's instructions. Polyclonal (Pabp68) and monoclonal (P68-RGG) antibodies against p68 were the same as previously reported (Yang et al., 2005). Antibodies HA-tag, GAPDH, Lamin A/C, CaM, α-tubulin, β-tubulin, heavy chain of kinesin-1, Dynein intermediate 1, and β-actin were purchased from Cell Signaling, Abnova, SantaCruz, Abcam, and AnaSpec respectively.

Immunopurification of HA-tagged proteins from cell extracts: SW480 cells expressing HA-tagged proteins by transient transfection were cultured in medium L-15 with 10% FBS. The cells were subjected to different treatment (such as scratchwounds). The cells were collected and lysed in NETS buffer with addition of the protease inhibitors. To minimize the non-specific protein-protein interactions in the immunopurification, 600 mM (final concentration) 6-aminocaproic acid (6-AcA) along with 800 mM (final concentration) NaCl were added to the extracts and incubated for 2 hours at RT. A commercially available polyclonal anti-HA antibody was added to the prepared extracts (500 μl extracts/ 20 μl of Abs). The mixture was incubated overnight at 4° C. After incubation, the protein G agarose beads (50 μl, pretreated with BSA 3 mg/ml) were then added to the mixture and incubated for an additional 2 hours. The beads were washed in NETS buffer 6 times. The beads bound proteins were either directly used in some assays (such as ATPase assays) or the bound HA-tagged proteins were eluted using the HA peptide. The beads with bound proteins were suspended in elution buffer and packed in a small column. The HA peptide (Sigma) (500 μg/ml in elution buffer) was flowed through the column to elute the bead bound proteins. The fractions were collected and analyzed by SDS-PAGE and immunoblot to identify the fractions that contained HA-tagged protein. The eluted proteins were further dialyzed in the subsequent assay buffers (such as MT binding buffer) and concentrated by centrifugation.

Metastasis inhibition of SW620 xenograft and orthotopic 4T1 tumors: All animal experiments were carried out in accordance with the guidelines of IACUC of Georgia State University. Nude mice or Balb/c mice (6 to 7 weeks old, Harlan Laboratory) were subcutaneously or orthotopically injected with $5\times10^6$ SW620 or $2\times10^6$ 4T1 cells. Peptides at appropriate doses were administered to the tumor bearing mice by intraperitoneal (i.p.) injection at appropriate time intervals. Tumor formation and volumes were assessed every 2 days. Tumor volumes were measured by two perpendicular diameters of the tumors over a 4-week time course with the formula $4p/3\times(width/2)^2\times(length/2)$. The tumors and organs were collected and weighed at the end of the experiments. Tissue sections were prepared from harvested tumors and organs. Tissue sections were analyzed by either H&E or immune staining. For metastasis analyses of SW620 tumors, tissue extracts were prepared from spleens, total RNAs were extracted from the tissue extracts. RT-PCRs were performed with the isolated RNAs. For metastasis of 4T-1 cells, lung and liver were inspected.

Results

A p68 peptide fragment containing Y593 a.a. was examined for the ability to inhibit EMT (by competing with the Y593 phosphorylated p68), since inhibiting EMT is an indication that it may be useful for metastasis intervention. Three peptides were synthesized. The first two peptides contained amino acids 584 to 602 of p68 with Y593 phosphorylation ("PepPhoY593") and without ("PepY593") Y593 phosphorylation, respectively. The third peptide contained amino acids 549-568 of p68, containing an IQ motif ("PepIQ"). Both the PepIQ and PepY593 were used as control peptides. The three peptides were fused with a TAT cell permeable sequence at the N-terminus (see Table 4 for sequences).

The peptides were used to treat a nude mice xenograft of SW620 cells at dose of 2 mg/kg (i.p. daily dose for two weeks). SW620 cells were used because they contain high p68 Y593 phosphorylation (Carter, C L, et al. *Oncogene* 29:5427-5436 (2010); Yang, L, et al. *Mol Cancer Res* 3:355-363 (2005)). It is well established that the xenograft of SW620 will metastasize to lymph nodes, and the metastasis can be analyzed by examination of SW620 cells in the spleen (Liu, K, et al. *J Immunol* 171:4164-4174 (2003)).

Figure 1B:
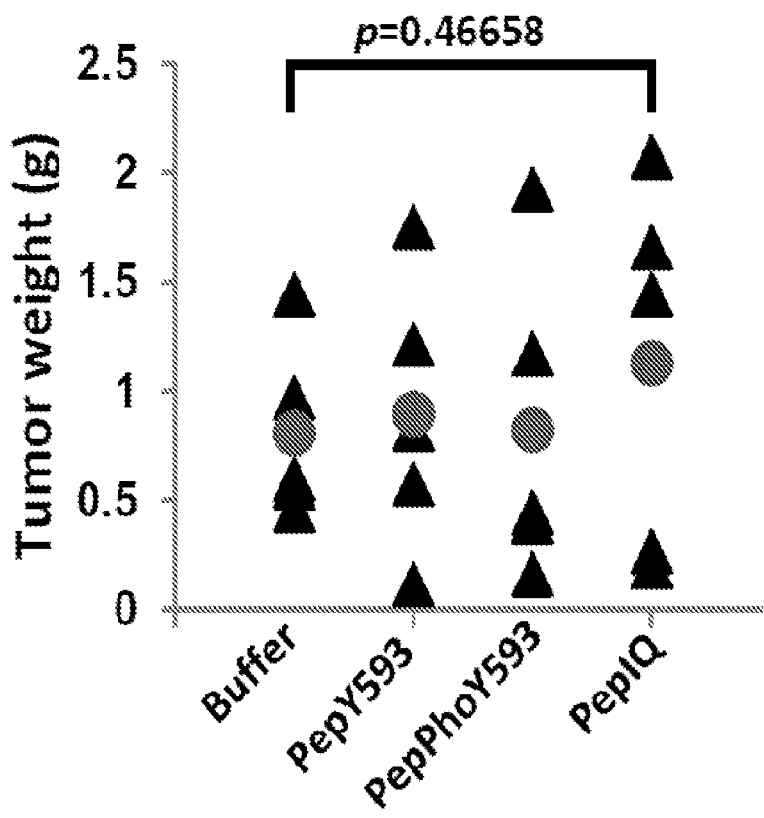
FIG. 1B is a plot showing tumor weight (g) of SW620 tumors harvested from mice after 28 days growth with 14 days treatment using buffer (column 1), PepY593 peptide (column 2), PepPhoY593 (column 3), or PepIQ (column 4).
Figure 1C:
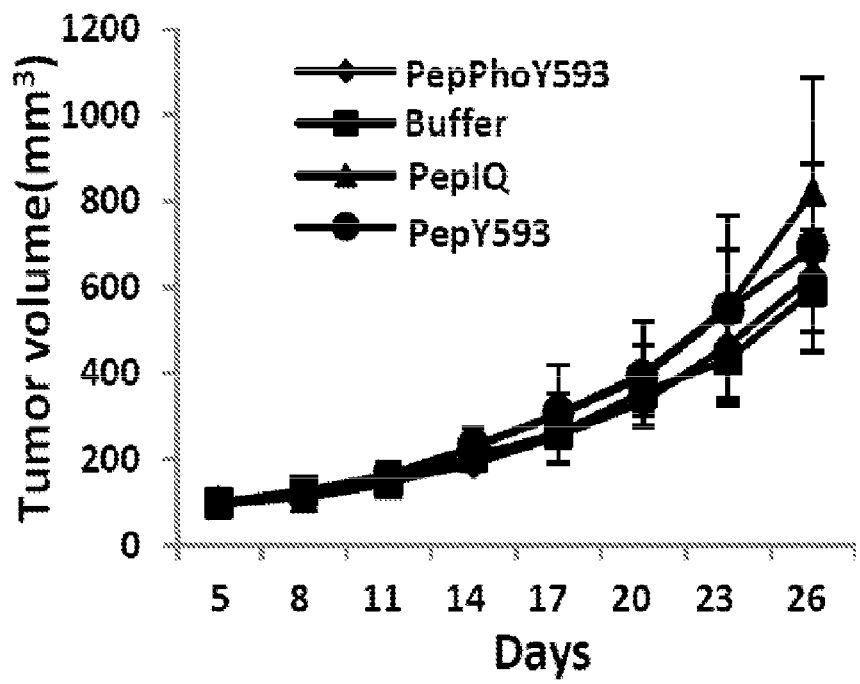
FIG. 1C is a graph showing tumor volume ($mm^3$) of SW620 tumors as a function of time after treatment using buffer (-■-), PepY593 peptide (-●-), PepPhoY593 (-♦-), or PepIQ (-▲-) calculated by formula: Tumor volume=π/6× (width) 2×length.
Figure 1D:
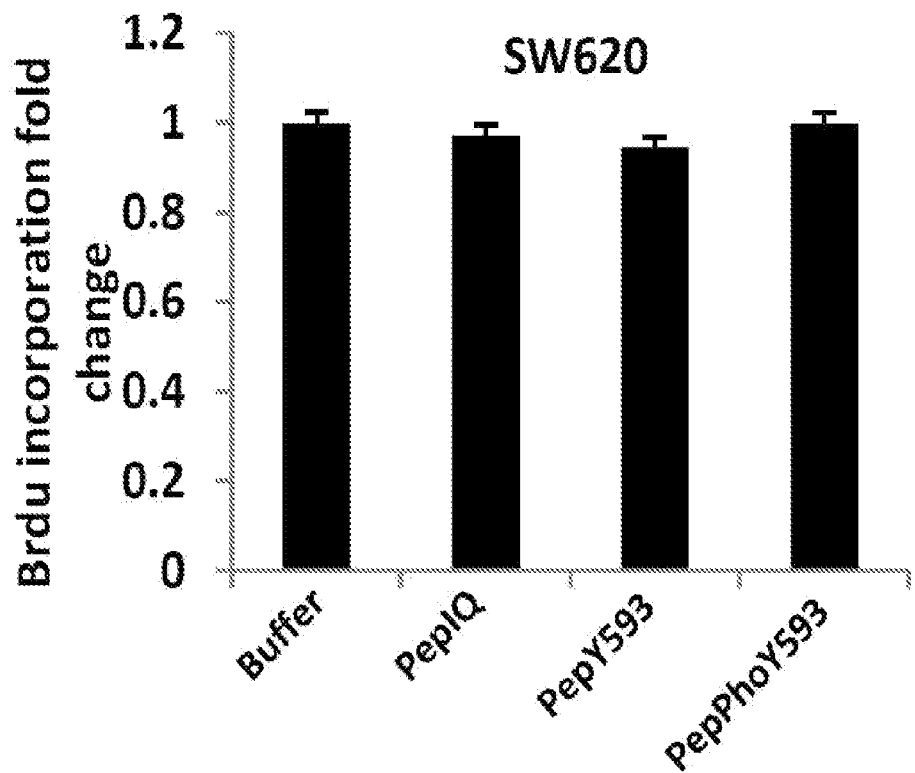
FIG. 1D is a bar graph showing BrdU incorporation (fold change after 48 hours of culture) in SW620 cells treated with buffer (column 1), PepIQ (column 2), PepY593 peptide (column 3), or PepPhoY593 (column 4).

The PepPhoY593 peptide had almost no effects on the SW620 metastasis (Table 1), while the cancer metastasis was largely diminished by the PepIQ peptide (FIG. 1A). The tumor growth rate was not significantly affected by the treatment with any of the peptides as demonstrated by tumor growth and immunostaining using the antibody against Ki-67 (FIGS. 1B, and 1C). Consistently, the peptides had no effects on SW620 cell proliferation in vitro (FIG. 1D).

Figure 6:
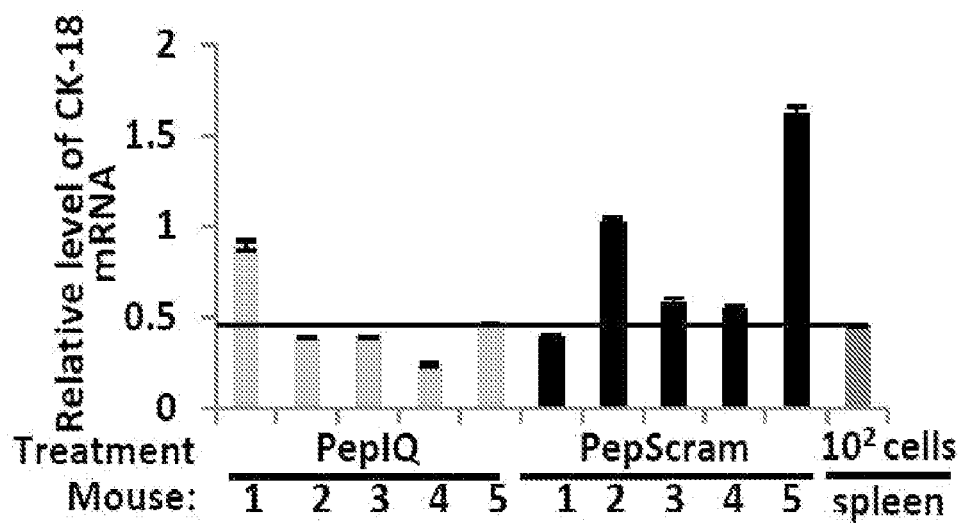
FIG. 6 is a bar graph showing human CK-18 mRNA levels (quantitative RT-PCR, relative to β-actin) from the spleen extracts of mice with xenograft of SW620 tumors that were treated with PepIQ (columns 1-5) or PepScram (columns 6-10), or from spleen harvested from mice without tumor implantation but with direct injection of 100 SW620 cells ($10^2$ cells/spleen).

We also examined whether the peptides would abolish PDGF stimulated EMT by analyzing the cellular levels of EMT markers, E-cadherin and vimentin. Treatment with the PepPhoY593 peptide led to a decrease in vimentin and an increase in Ecadherin. However, the levels of E-cadherin and vimentin were not significantly affected by the treatment of PepIQ and PepY593. These results indicate that the PepPhoY593 peptide had no effects on cancer metastasis, while the PepIQ inhibited the metastasis. These results also indicate that the inhibitory effect was not due to inhibition on cell proliferation and EMT. The effect of the PepIQ peptide on cancer metastasis was confirmed by an additional treatment using the PepIQ and a control peptide with a scrambled sequence (PepScram) (FIG. 6, Table 2, Table 4).

TABLE 2

Effects of PepIQ Sequence on Tumor Metastasis

| Treatment | PepIQ | PepScram |
|---|---|---|
| Metastasis rate | 2/5 | 4/5 |

Figure 7A:
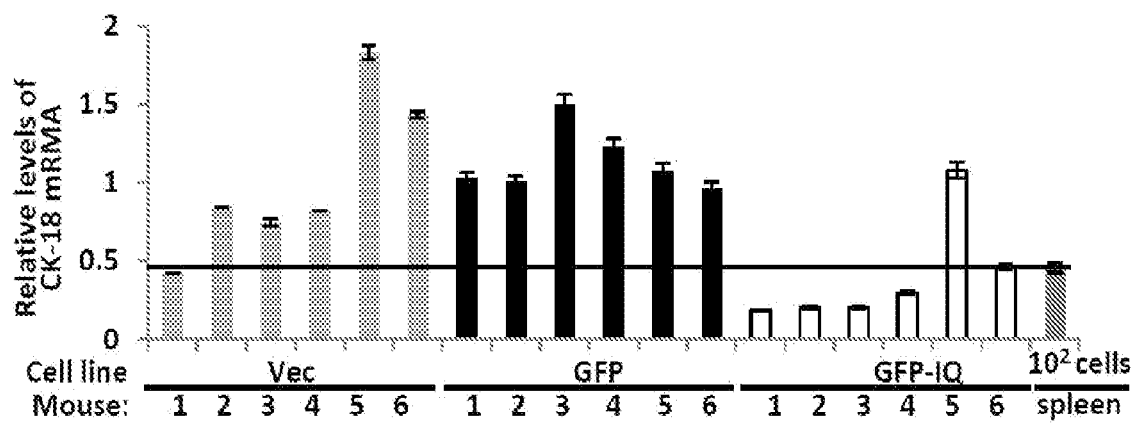
FIG. 7A is a bar graph showing human CK-18 mRNA levels (quantitative RT-PCR, relative to β-actin) from 1) the spleen extracts of mice with xenograft of SW620 tumors that were transfected with empty vector (Vec) (columns 1-6) or with a vector expressing eGFP (columns 7-12) or a fusion protein containing a p68 peptide fragment spanning aa 584-602 fused to the C-terminus of eGFP ("eGFP-IQ," SEQ ID NO:6) (columns 13-18), or 2) from spleen harvested from mice without tumor implantation but with direct injection of 100 SW620 cells ($10^2$ cells/spleen).
Figure 7B:
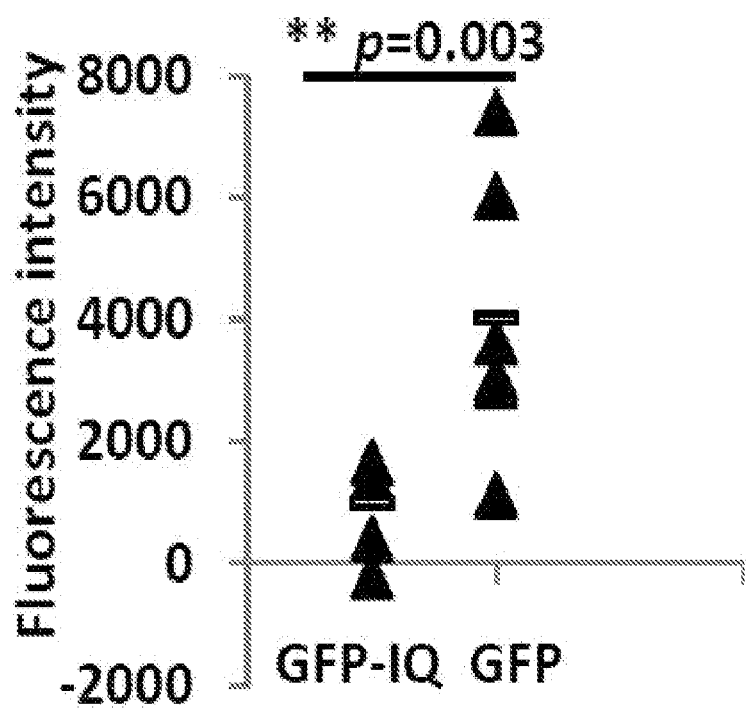
FIG. 7B is a plot showing fluorescence intensities (arbitrary units) of mouse spleens harvested from mice that carry tumors of SW620 cells transfected with a vector expressing eGFP-IQ (column 1) or eGFP (column 2).
Figure 7C:
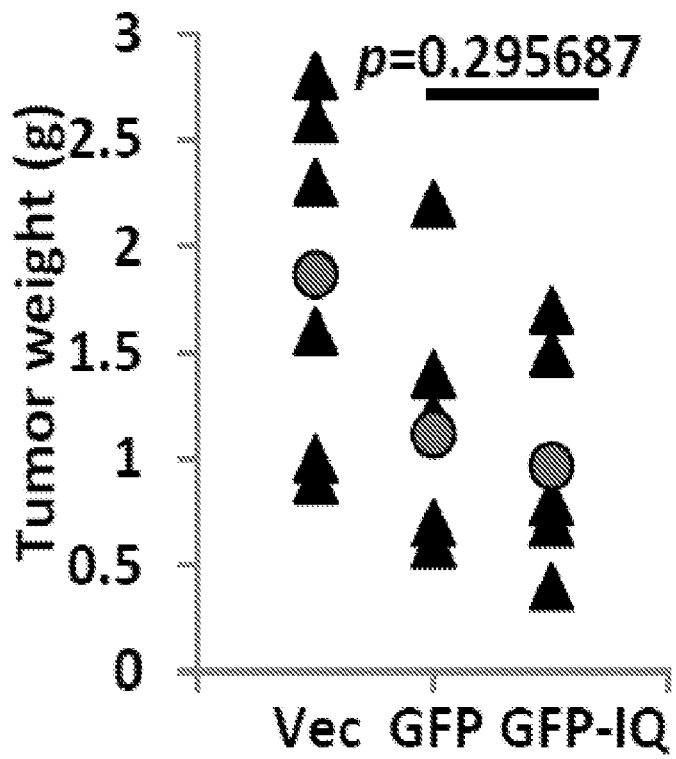
FIG. 7C is a plot showing tumor weight (g) of harvested SW620 tumors transfected with empty vector (Vec) (column 1) or with a vector expressing eGFP (column 2) or eGFP-IQ (column 3) after 28 days growth.

A fusion protein containing amino acids 549-568 of p68 fused to the C-terminus of eGFP ("eGFP-IQ") (see Table 4 for sequences) was expressed in SW620 cells to confirm the effects of the PepIQ sequence on inhibiting cancer metastasis. Expression of the eGFP-IQ greatly reduced the cancer metastasis of the SW620 xenograft, while the metastasis reduction was not observed with expression of eGFP as a control or buffer alone (FIGS. 7A, 7B, Table 3). The reduction of the cancer metastasis was not due to changes in tumor growth upon the expression of the fusion proteins (FIG. 7C).

TABLE 1

Effects of PepIQ Sequence on Tumor Metastasis

| Treatment | Buffer | PepY593 | PepPhoY593 | PepIQ |
|---|---|---|---|---|
| Metastasis rate | 5/5 | 5/5 | 3/5 | 1/5 |

TABLE 3

Effects of eGFP-IQ Sequence on Tumor Metastasis

| Cell line | Vec | eGFP | eGFP-IQ |
|---|---|---|---|
| Metastasis rate | 5/6 | 6/6 | 2/6 |

TABLE 4

Sequences

| | | | | |
|---|---|---|---|---|
| Human p68 | MSGYSSDRDR | GRDRGFGAPR | FGGSRAGPLS | SEQ ID NO: 1 |
| | GKKFGNPGEK | LVKKKWNLDE | LPKFEKNFYQ | |
| | EHPDLARRTA | QEVETYRRSK | EITVRGHNCP | |
| | KPVLNFYEAN | FPANVMDVIA | RQNFTEPTAI | |
| | QAQGWPVALS | GLDMVGVAQT | GSGKTLSYLL | |
| | PAIVHINHQP | FLERGDGPIC | LVLAPTRELA | |
| | QQVQQVAAEY | CRACRLKSTC | IYGGAPKGPQ | |
| | IRDLERGVEI | CIATPGRLID | FLECGKTNLR | |
| | RTTYLVLDEA | DRMLDMGFEP | QIRKIVDQIR | |
| | PDRQTLMWSA | TWPKEVRQLA | EDFLKDYIHI | |
| | NIGALELSAN | HNILQIVDVC | HDVEKDEKLI | |
| | RLMEEIMSEK | ENKTIVFVET | KRRCDELTRK | |
| | MRRDGWPAMG | IHGDKSQQER | DWVLNEFKHG | |
| | KAPILIATDV | ASRGLDVEDV | KFVINYDYPN | |
| | SSEDYIHRIG | RTARSTKTGT | AYTFFTPNNI | |
| | KQVSDLISVL | REANQAINPK | LLQLVEDRGS | |
| | GRSRGRGGMK | DDRRDRYSAG | KRGGFNTFRD | |
| | RENYDRGYSS | LLKRDFGAKT | QNGVYSAANY | |
| | TNGSFGSNFV | SAGIQTSFRT | GNPTGTYQNG | |
| | YDSTQQYGSN | VPNMHNGMNQ | QAYAYPATAA | |
| | APMIGYPMPT | GYSQ | | |

TABLE 4-continued

Sequences

| | | |
|---|---|---|
| PepY593 | MHNGMNQQAYAYPATAAAP | SEQ ID NO: 2 |
| PepPhoY593 | MHNGMNQQA [p] YAYPATAAAP | SEQ ID NO: 3 |
| PepIQ | FVSAGIQTSFRTGNPTGAYG | SEQ ID NO: 4 |
| PepScram | FASGQINTFVSRGTPGYATG | SEQ ID NO: 5 |
| HA | GRKKRRQRRRG | SEQ ID NO: 6 |

[p] indicates phosphorylation of following amino acid

Example 2

The IQ Peptide Interrupts p68-CaM Interaction that is Essential for Cell Migration Materials and Methods Scratch-wound treatments: A scratch or multiple scratches using pipette tips were introduced into a 6 well cell culture plate. The cells were further cultured under serum starvation for 30 minutes, and were subsequently cultured for an additional indicated time. The scratch-treated cells were either directly visualized by microscopes or the cells were fixed and subsequently examined by immunostaining. Alternatively, the cells were collected and lysized. The prepared cellular extracts were then used for other analyses.

Boyden chamber assay: QCM™ 24-Well Fluorimetric Cell Migration Assay kit was used to measure the migration of SW480 cells. The test cells were first treated under the different conditions in regular cell culture plates. The treated cells were re-suspended into optimum medium (without serum) and seeded into the inner chamber of the migration assay kit. The L-15 culture medium with 10% FBS was added to the outer chambers. After overnight incubation, medium in the inner chamber was removed and the cells attached to the outer bottom side were detached using the cell detachment buffer (included in the kit). The detached cells were then lysed using the cell lysis buffer (included in the kit). The amounts of the migrated cells were determined by measuring the fluorescence using $\lambda ex=485$ nm and $\lambda em=535$ nm. The migration of the control cells with p68 knockdown was defined as 1.

Results

Figure 2:
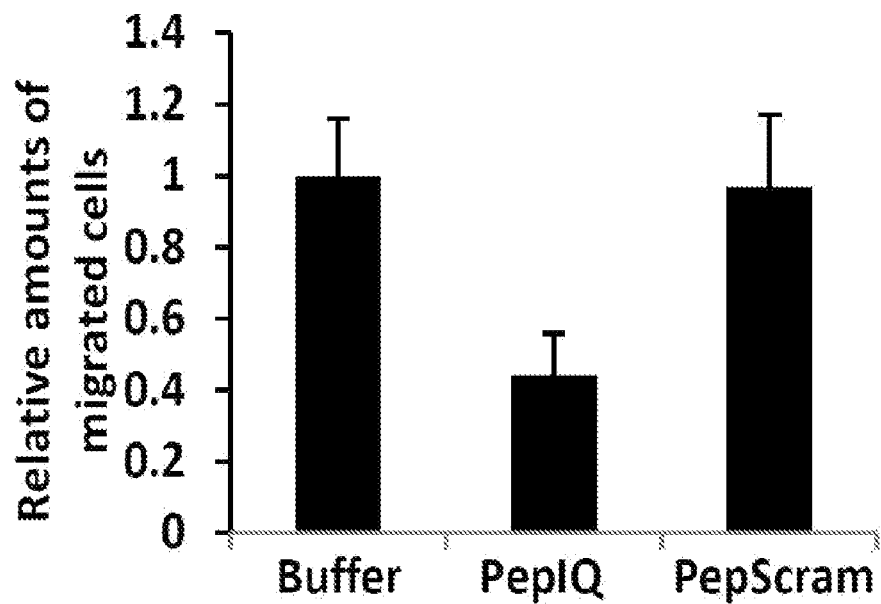
FIG. 2 is a bar graph showing cell migration in a Boydon Chamber assay (relative to buffer control) of SW480 cells treated with buffer (column 1), PepIQ (column 2), or a scrambled peptide with TAT ("PepScram," SEQ ID NO:5) (column 3).
Figure 7D:
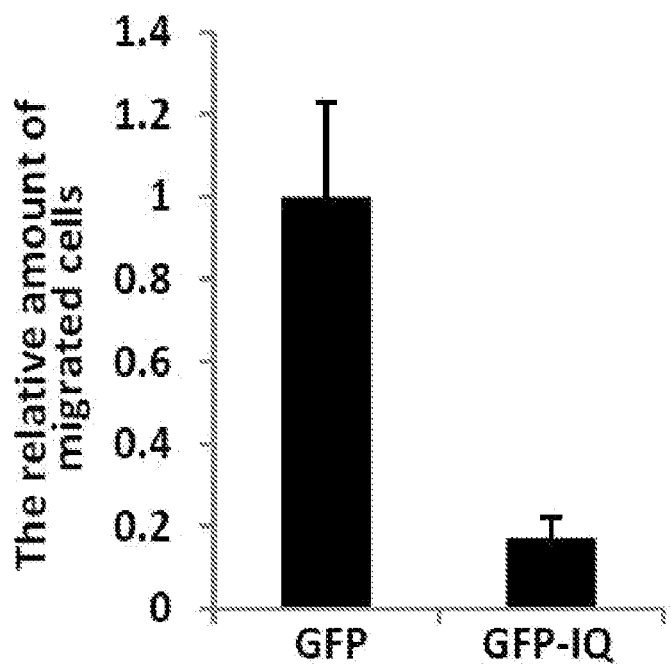
FIG. 7D is a bar graph showing cell migration by Boyden chamber assay (relative to eGFP control) of SW480 cells transfected with a vector expressing eGFP (column 1) or eGFP-IQ (column 2). p values were calculated by pairwise student t-test.

The preceding experiments showed that the peptide treatments had no effects on expression of EMT markers or on tumor growth and cell proliferation. Cell migration may be the target of the IQ peptide. SW480 cells have similar migration properties with much lower proliferation rate compared to SW620 cells. Cell migration was almost completely inhibited by the PepIQ in the migration assays (FIG. 2). Similarly, cell migration was also dramatically inhibited by stable expression of the eGFP-IQ in SW480 cells (FIG. 7D).

p68 interacts with CaM in a number of in vitro binding studies, and the IQ motif harbors the p68-CaM interaction site. PepIQ and eGFP-IQ competed with p68 to interact with CaM in the cells, and therefore inhibited cell migration.

CaM beads pull-down assay was used to determine whether the PepIQ peptide affected the p68 and CaM interaction. In these experiments, peptide treatment did not lead to dramatic changes in the p68-CaM interaction. Thus, the p68-CaM interaction was examined under migration stimuli by co-immunoprecipitation with extracts of SW480 cells using an antibody against CaM. A strong increase in the p68 and CaM co-immunoprecipitation was observed in the SW480 cells that were subjected to multiple scratch-wound treatments, and the extent of increase was dependent upon the number of scratches introduced. Similarly, there was a strong increase in the p68 and CaM co-precipitation upon the EGF treatment.

Figure 8:
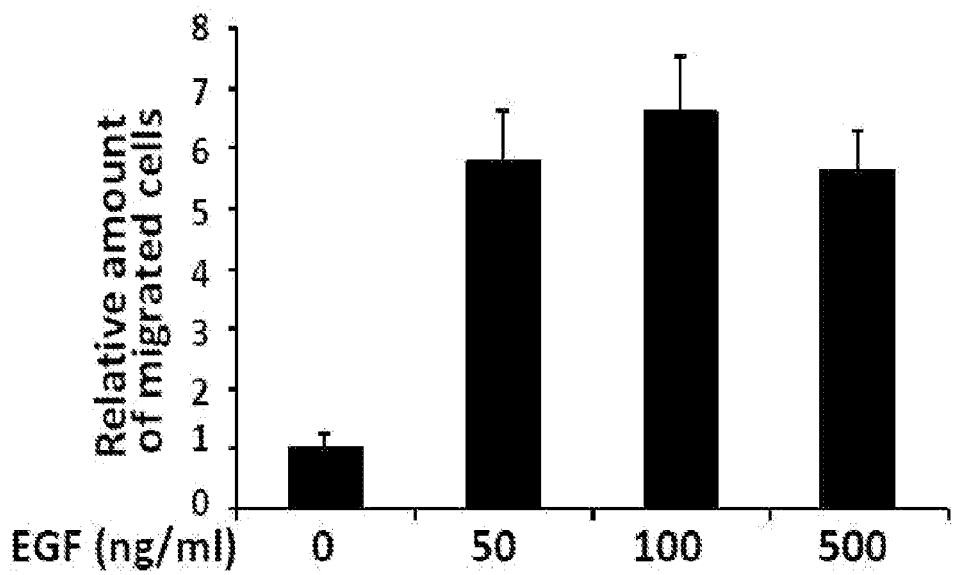
FIG. 8 is a bar graph showing cell migration by Boyden chamber assay (relative to control) of SW480 cells treated with EGF at 0 ng/ml (column 1), 50 ng/ml (column 2), 100 ng/ml (column 3), or 500 ng/ml (column 4).

Measurement of the changes in cell migration revealed a close correlation between the increase in the p68-CaM interaction and cell migration under the stimulation of EGF (FIG. 8). These results indicate that cell migration strengthened the p68-CaM interaction.

To test whether the PepIQ abolished the enhancement of the p68-CaM interaction induced by cell migration, the p68-CaM interaction was probed in cell lysate of SW480 cells that were treated by the peptide. In these experiments, the strong increase in the p68-CaM interaction upon multiple scratch wound was not observed with cells that were treated by the peptide. Similarly, the p68-CaM interaction was not dramatically strengthened upon migration stimuli in SW480 cells in which the eGFP-IQ was expressed. However, an increase in CaM and eGFP-IQ co-precipitation was detected from extracts of the scratch wound cells, indicating that the eGFP-IQ competed with p68 for CaM interaction.

To test whether the PepIQ peptide disrupted the interaction of IQGAP1 or Myosin-II with CaM, cell extracts of SW480 cells that were treated by the PepIQ with/without multiple scratch-wound were co-immunoprecipitated using the antibody against CaM. Immunoblots of the co-precipitates indicated that the IQGAP1-CaM and Myosin-CaM interactions were not affected by the PepIQ treatment regardless whether or not the cells were treated by the scratch wound. The results indicate that the PepIQ peptide likely disrupts the p68 and CaM interaction specifically. The results also excluded a possibility that the PepIQ sequestered all CaM in the cells therefore inhibited cell migration. Thus, these experiments supported the notion that cell migration strengthened the p68-CaM interaction, and the IQ peptide disrupted the p68-CaM interaction induced by migration, thereby inhibiting cell migration.

Figure 3A:
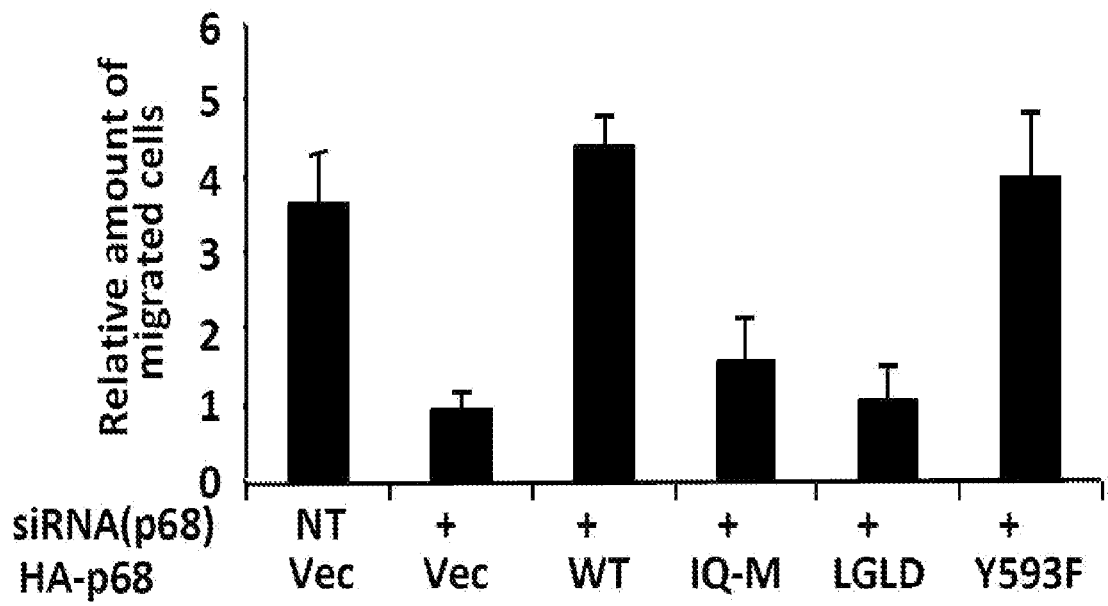
FIG. 3A is a bar graph showing cell migration in a Boydon Chamber assay (relative to buffer control) of SW480 cells expressing 1) treated with RNAi targeting p68 ("+" for "siRNA(p68)") or non-target RNAi ("NT") and 2) transfected with empty vector (Vec) or with a vector expressing an hemagglutinin (HA)-tagged p68 ("HA-p68") where the p68 is wild type ("WT") or it contains a mutation in IQ motif ("IQ-M"), an ATPase activity deficiency mutation ("LGLD"), or a Y593F mutation.

Endogenous p68 was knocked down in SW480 cells, and HA-tagged wild-type p68 peptide ("WT"), IQ-M peptide, LGLD peptide (An ATPase activity deficiency mutant with an R403L mutation (Lin C, et al. *Mol Cell Biol* 25:7484-7493 (2005)), or Y593F mutant p68 peptide (Yang L, et al. *Cell* 127:139-155 (2006)), was expressed in the cells. Boyden chamber assays showed that knockdown of p68 resulted in dramatic reduction in cell migration and the cell migration could be fully recovered by expression of WT p68, but not by the IQ-M mutant. As a control, the cell migration could also be recovered by expression of a mutant that carries mutation at an irrelevant site (Y595F) (FIG. 3A). Interestingly, expression of an ATPase deficient p68 (LGLD) in the p68 knockdown cells did not recover cell migration, indicating that the ATPase activity of p68 is required for cell migration (FIG. 3A).

Figure 3B:
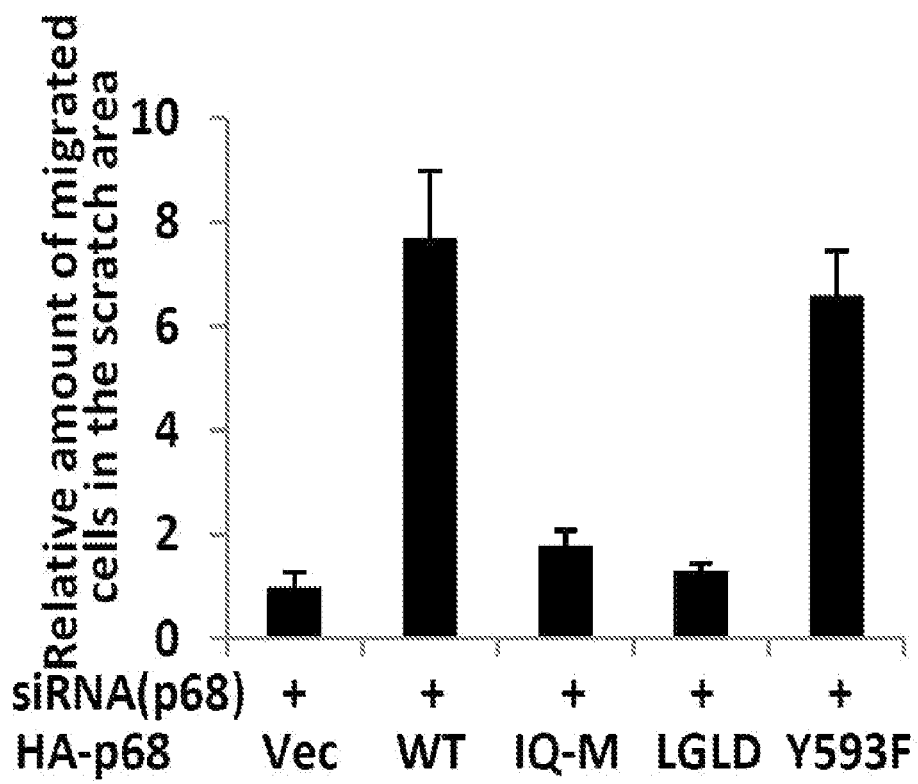
FIG. 3B is a bar graph showing migration (relative amount in a fixed microscopic area after scratch wounding) of SW480 cells treated with siRNA(p68) and transfected with empty vector (Vec) or a vector expressing WT, IQ-M, LGLD, or Y593F HA-p68s.

The functional role of the p68 and CaM interaction in cell migration was further confirmed by the scratch-wound assays (FIG. 3B). Immunofluorecence staining of the exogenously expressed HA-p68 and mutants using anti-HA antibody revealed that no cells expressing HA-IQ-M and HA-LGLD migrated to the wounds, while p68 WT-expressing cells migrated to the wound areas normally. These experiments showed that the p68-CaM interaction is required for cell migration.

Example 3

The p68 and CaM Interaction Affect the Localization of Both CaM and p68 to the Cytoplasm and to the Leading Edge of the Migrating Cells A strong cytoplasm p68 staining was observed only in the migrating cells. When the cells reached the migration destination, p68 re-localized exclusively back to the cell nucleus. Second, there were very high levels of p68 staining in the cytoplasm and at the leading edge of the migration cells and this staining pattern was not observed in the non-migrating cells. Since p68 interacted with calmodulin in migration cells, p68 and calmodulin were expected to exhibit similar localization patterns. To this end, scratch-wound was introduced to SW480 cells. The cells were then analyzed by immunostaining. In these experiments, p68 and calmodulin co-localized, especially at the leading edge of the migration cells. In the non-migrating cells, p68 localized exclusively in the nucleus, while calmodulin could be detected almost everywhere in the cells. However, there were significant increases in calmodulin levels at the cell migration leading edges and the nucleus in the migration cells compared to that in non-migration cells.

The localization patterns of exogenously expressed HA-p68 mutants LGLD and IQ-M and the effects of their expression on the cellular localization of CaM were examined under scratch-wound conditions. The endogenous p68 was knocked down. The HA-p68s, WT, LGLD, or IQ-M peptides were expressed in p68 knockdown cells. Scratch-wound was subsequently introduced. Immunostaining using anti-HA antibody showed that the exogenously expressed WT HA-p68 localized to the leading edge of migrating cells. The ATPase deficiency mutant LGLD, although detected in the nucleus and the cytoplasm, failed to accumulate at the membrane edge. Interestingly, the IQ-M almost exclusively localized in the cell nucleus. Immunostaining of CaM in the same HA-p68s expressing cells revealed that CaM also failed to accumulate at the membrane edge of the cells that expressed LGLD or IQ-M mutant under the scratch-wound condition. The results indicated that the p68-CaM interaction and the ATPase activity of p68 were required for the localization of CaM to the leading edge during cell migration.

Example 4

P68 RNA Helicase Exhibits a CaM-Dependent Microtubule Motor Activity

Materials and Methods

Microtubule pull-down and gliding assay: Microtubule was reconstituted in warm PM buffer (15 mM Pipes pH 7.0, 1 mM $MgCl_2$) with the addition of taxol as instructed by the vendor. The MTs were ready to use after 15 minutes incubation at room temperature. The test protein(s) was incubated with the reconstituted MTs under various conditions. The MTs with the bound proteins were separated from the incubation solution by centrifugation at 100,000 g for 30 minutes. Co-precipitates with the MTs were re-suspended in 50 μl of 2×SDS PAGE loading buffer and heated to 85° C. for 10 minutes and subsequently analyzed by immunoblots. The HA-p68-CaM, HA-p68, or His-p68-CaM peptide (10 μl) was loaded onto a glass slide. The slide was blocked with the blocking buffer. For the slide loaded with HA-p68, 10 μl of calmodulin with 0.5 mM of $Ca^{2+}$ was added to the slide and was incubated for 10 minutes. After loading the slide was washed with the $Ca^{2+}$ containing wash buffer to remove the unbound proteins. The prepared Rodamine labeled microtubules were then loaded onto the slide. The same $Ca^{2+}$ containing wash buffer was used to remove unbound microtubules. The movement of microtubules was then recorded by the confocal microscope.

Calmodulin beads pull-down: Whole cell lysate from SW480 cells was prepared as previously described (Yang L, et al. *Cell* 127:139-155 (2006); Yang L, et al. *Mol Cancer Res* 3:355-363 (2005)). The agarose beads conjugated with recombinant calmodulin (Abcam) were pre-washed with Ca2+ containing buffer (2 mM CaCl2, 50 mM NaCl in 50 mM Tris-HCl pH 7.5) or EGTA containing buffer (5 mM EGTA, 50 NaCl in 50 mM Tris-HCl pH 7.5). After washing, the beads were incubated with the whole cell lysates in the $Ca^{2+}$ containing or EGTA containing buffer. The beads were extensively washed after incubation. Finally, 2× SDS-loading buffer were added to the beads and the beads were heated to 85° C. for 10 minutes. The proteins that were pulled down by the CaM beads were analyzed by 10% SDS PAGE and subsequent immunoblot.

ATPase assays: The ATPase activity of different proteins was assayed by an experimental procedure similar to that described previously (Huang Y, et al. *J Biol Chem* 277: 12810-12815 (2002); Lin C, et al. *Mol Cell Biol* 25:7484-7493 (2005)) with minor modifications. The reaction volume was 50 μl, containing 4 μg of MTs (or 2 μg of RNA), 4 mM ATP, and 0.5 mM $Ca^{2+}$ or 5 mM EGTA in the ATPase assay buffer (10 mM Pipes pH 7.0, 1 mM $MgCl_2$, 25 mM NaCl with taxol added). 10 μl of the purified HA tagged proteins (bound or un-bound to agarose beads) was added. The ATPase reactions were incubated for 30 minutes at 37° C. After incubation, 30 μl of the supernatant was added to 1 ml of malachitegreen-molybdenum reagent. After 5 minutes incubation at room temperature, the absorbance of the reaction was then measured at 630 nm (A630). The concentrations of released inorganic phosphate were determined by matching the $A_{630nm}$ in a standard curve of $A_{630nm}$ vs known phosphate concentrations.

Results

In order to determine whether p68 mediates CaM and microtubule motor interactions in the migrating cells, interactions between p68 and two well known microtubule motor molecules, kinesin and dynein, were probed by co-immunoprecipitation in cell extracts prepared from SW480 cells that were treated by multiple scratch-wounds.

Co-precipitation experiments were conducted with exogenously expressed HA-p68 that was immunopurified from lysates of SW480 cells with/without multiple scratch-wound treatments. The purified HA-p68 was incubated with microtubule. After precipitation of the microtubule by centrifugation, the presence of the HA-p68 in the microtubule precipitates was examined by immunoblot using an anti-HA antibody. HA-p68 that was purified from cells that were treated by scratch-wounds co-precipitated with the microtubule in the presence of CaM. In the contrary, HA-p68 immunopurified from SW480 cells that were not treated by scratch-wounds did not co-precipitate with the microtubule even in the presence of CaM. The HA-p68 did not co-precipitate with unpolymerized α- and β-tubulin in the presence and absence of $Ca^{2+}$ and CaM. Interestingly, co-precipitation of HA-p68 with microtubule in the presence of CaM was completely $Ca^{2+}$ dependent, while the ATP was dispensable as the HA-p68 co-precipitated with the microtubule in the presence and absence of ATP, and in the presence of non-hydrolysable ATP analogue AMP-PNP.

Figure 9:
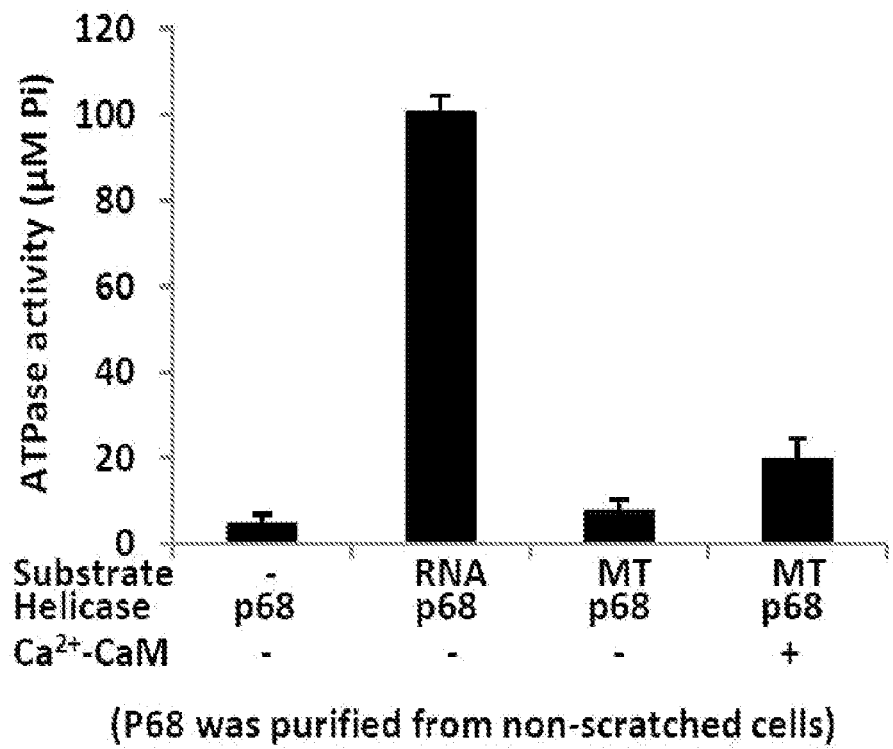
FIG. 9 is a bar graph showing ATPase activity (μM inorganic phosphate hydrolyzed from ATP) of HA-p68 that was immunopurified from cell lysates of SW480 cells (no scratch wound treatment) in the presence of no substrate (column 1), RNA substrate (column 2) or MT substrate (columns 3-4), and optimally in the presence of 0.5 mM $CaCl_2$ ($Ca^{2+}$) (column 4).

The interaction of p68-CaM with the microtubule was further examined by binding of rhodamine label microtubule activity (LGLD) also abolished the microtubule stimulated ATPase activity of the protein (FIG. 9). In addition, this microtubule-dependent ATPase activity was not detected with the HA-p68 purified from the cells extracts without scratch-wound treatment (FIG. S4C).

HA-p68 was purified from SW480 cells with/without scratch-wound treatment and attached to a glass slide. Rhodamine-labeled microtubule was then added to the glass slide. Migration of the microtubule in the presence and absence of ATP was then recorded. First, migration of microtubule was clearly visualized with the positive control motor protein kinesin. Migration of the microtubule on the glass slide with HA-p68 attached was also clearly evident in the presence of CaM and $Ca^{2+}$. In contrary, the migration of the microtubule was not observed on the glass slide with HA-p68 that purified from SW480 cell extracts without scratch-wound treatment. As a negative control, the migration was not observed without addition of ATP. Statistical analyses indicated that HA-p68/CaM exhibited motor activity on the microtubule very similar to that of a control motor protein kinesin (the number of gliding microtubles, mean gliding speed, and maximum gliding speed in a random selected group of 50 were similar) (Table 5).

TABLE 5

Summary of quantitative analysis of the movements of Rhodamine labeled microtubles in gliding assays

|  | Kinesin (ATP) | p68/$Ca^{2+}$-CaM (no ATP) | p68/$Ca^{2+}$-CaM (ATP) | His-p68-CaM (ATP) |
|---|---|---|---|---|
| % of gliding microtubules# (n = 50) | 89.20 ± 1.13 | 5.79 ± 3.13 | 74.15 ± 1.20 | 85.48 ± 2.40 |
| Mean gliding speed* (μm/min) | 0.17 ± 0.06 | 0.00 ± 0.00 | 0.16 ± 0.12 | 0.09 ± 0.03 |
| Maximum gliding speed (μm/min) | 0.27 ± 0.12 | 0.01 ± 0.00 | 0.52 ± 0.14 | 0.13 ± 0.02 |

Only MTs with gliding speed >0.025 μM/min were counted.
*Mean gliding speed only measure the MTs with the motility >0.05 μM/min.

to HA-p68 that was fixed on a glass slide. Binding of the microtubule to the glass slide was then visualized by fluorescence microscope. In these experiments, microtubule bound to HA-p68 peptide purified from scratch-wound treated SW480 cells in the presence of CaM and $Ca^{2+}$. The microtubule did not bind to HA-p68 without addition of CaM. The microtubule also did not bind to HA-p68 that was purified from SW480 cells that were not treated by scratch-wounds. The co-localization of exogenously expressed DsRed-p68 with microtubule labeled by eGFP was further examined. Under scratch-wound treatment, DsRed-p68 co-localized with eGFP labeled microtubule. Thus, p68 interacts with microtubule and the interaction is dependent upon the p68-CaM interaction.

Figure 4:
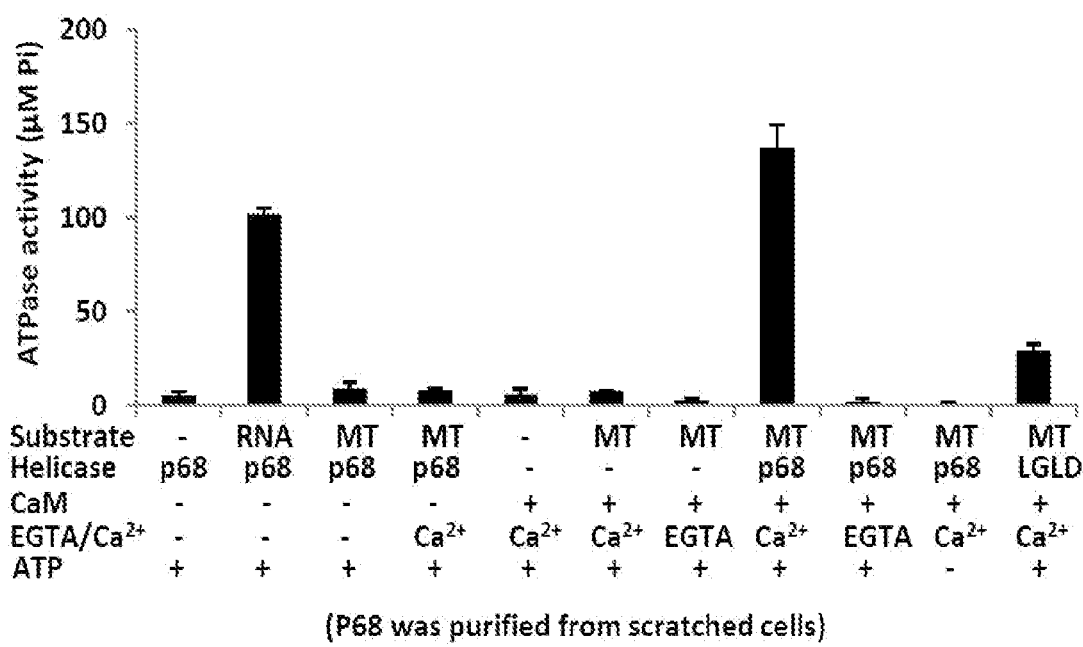
FIG. 4 is a bar graph showing ATPase activity (μM inorganic phosphate hydrolyzed from ATP) of control (columns 5-7), HA-p68 WT (columns 1-4, 8-10) or LGLD (column 11) immunopurified from cell lysates of SW480 scratch wound assays in the presence of 1) control (columns 1 and 5), RNA extracts from yeast (column 2) or in vitro assembled microtubule (MT) (columns 3-4, 6-11) substrates, 2) in the presence of control (columns 1-3), 0.5 mM $CaCl_2$ ($Ca^{2+}$) (columns 4-6, 8, 10-11) or 5 mM EGTA (EGTA) (10 and 12), and 3) in the presence (columns 5-11) or absence (columns 1-4) of the recombinant CaM.
Figure 10A:
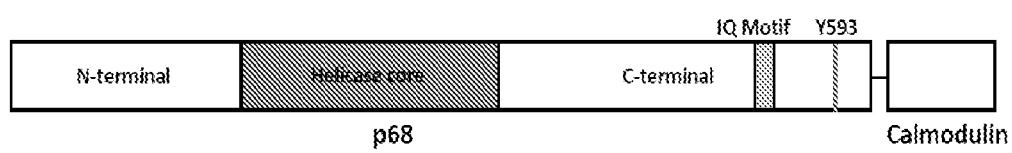
FIG. 10A is a schematic illustration of the "p68-CaM" fusion protein that resembles the p68 and CaM interaction.
Figure 10B:
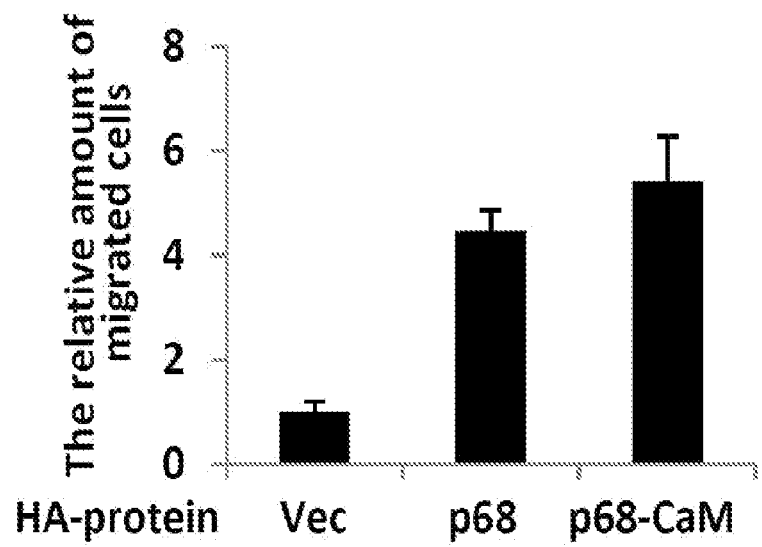
FIG. 10B is a bar graph showing cell migration by Boyden chamber assay (relative to Vec control) of SW480 cells treated with siRNA(p68) and transfected with a an empty vector (Vec) (column 1) or with a vector expressing p68 or p68-CaM.
Figure 10C:
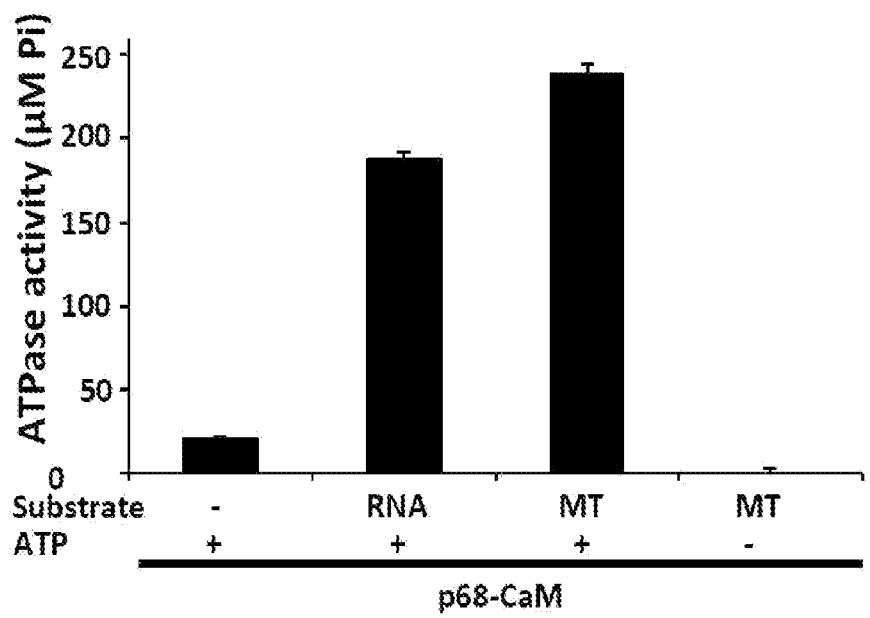
FIG. 10C is a bar graph showing ATPase activity (μM inorganic phosphate hydrolyzed from ATP) of Histidine-tagged p68-CaM in the presence of 1) no substrate (column 1), RNA substrate (column 2), or MT substrate (columns 3-4), 2) 0.5 mM $CaCl_2$ ($Ca^{2+}$), and 3) optionally in the presence of 4 mM ATP (columns 1-3).
Figure 11:
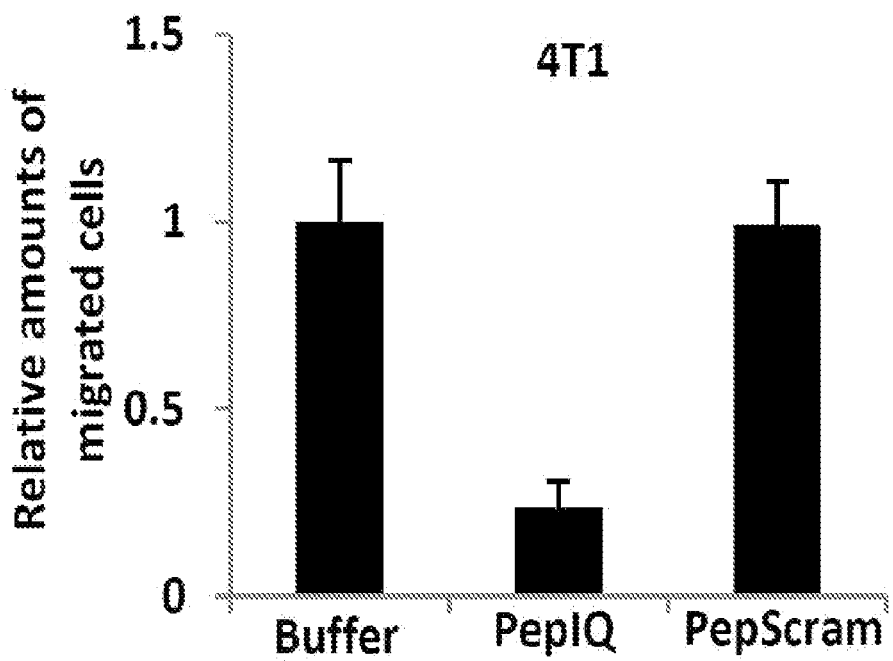
FIG. 11 is a bar graph showing cell migration by Boyden chamber assay (relative to control) of 4T1 cells treated with buffer control (column 1), PepIQ (column 2), or PepScram (column 3). Error bars are standard deviations

If p68 functions as a microtubule motor-like molecule, one would expect that microtubule would stimulate ATPase activity of p68. Thus, ATPase activity of the HA-p68 that was immunopurified from SW480 cells that were treated with multiple scratch-wound was analyzed in the presence of various possible substrates including RNA and microtubule. Interestingly, the protein demonstrated an even stronger microtubule stimulated ATPase activity (FIG. 4), and the microtubule stimulated ATPase activity was $Ca^{2+}$ dependent as addition of EGTA diminished the ATPase activity (FIG. 4). The observed microtubule-stimulated ATPase activity came from p68 as the mutation that abolishes p68 ATPase Since the p68 and HA-p68 peptides did not co-immunoprecipitate with two very common microtubule associated motor proteins, it is less likely that the observed HA-p68 motor activity is due to co-purification of other cellular motor proteins. To further exclude the possibility that the motor activity was due to contaminations during purification, a p68-CaM fusion protein was construct (illustrated in FIG. 10A). Expression of HA-p68-CaM fusion protein in SW480 cells led to greatly increased cell migration rates (FIG. 10B), and the expressed fusion protein localized to the leading edge of the migrating cells. In fact, expression of the fusion protein promoted formation of the lamellipodia/filopodia without scratch-wound treatment. These observations indicated that the fusion protein functionally resembled the p68-CaM interaction induced by cell migration signals. the fusion protein His-p68-CaM was then expressed and purified from bacterial *E. coli*. The gliding assay was performed with this bacterially expressed fusion protein. In these experiments, the bacterially expressed His-p68-CaM bound to microtubule, possesses microtubule dependent ATPase activity (FIG. 10C), and had strong microtubule motor activity (Table 5).

Finally, in order to determine whether p68 indeed migrated along microtubule in the cells that were induced for migration, p68 fused with DsRed ("DsRed-p68") and eGFP-labeled α-tubulin were exogenously co-expressed in SW480 cells. Cell migration was induced by scratch-wounds. Movement of the DsRed-p68 along the eGFP-labeled microtubule was recorded using confocal microscope with multi-photon excitation for imaging of living cells with time-lapse photography. The fluorescence images clearly indicated that p68 migrated along the microtubule under cell migration induction. The movements were toward the migration leading edge. The results indicate that by interacting with CaM, p68 RNA helicase can function as a microtubule motor.

Example 5

The PepIQ Inhibits Cancer Metastasis of an Orthotopic Model of 4T1 Cells

Figure 5A:
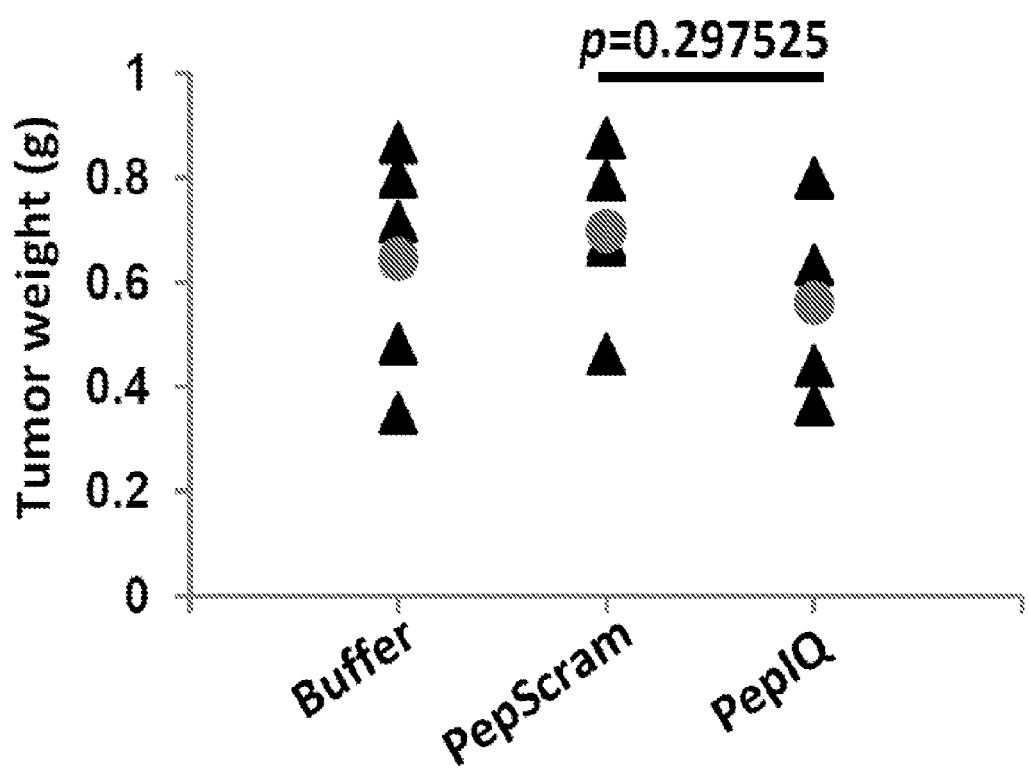
FIG. 5A is a plot showing tumor weight (g) of harvested 4T1 tumors after 26 days growth with 14 days treatment with buffer (column 1), PepScram (column 2), or PepIQ (column 3).
Figure 5B:
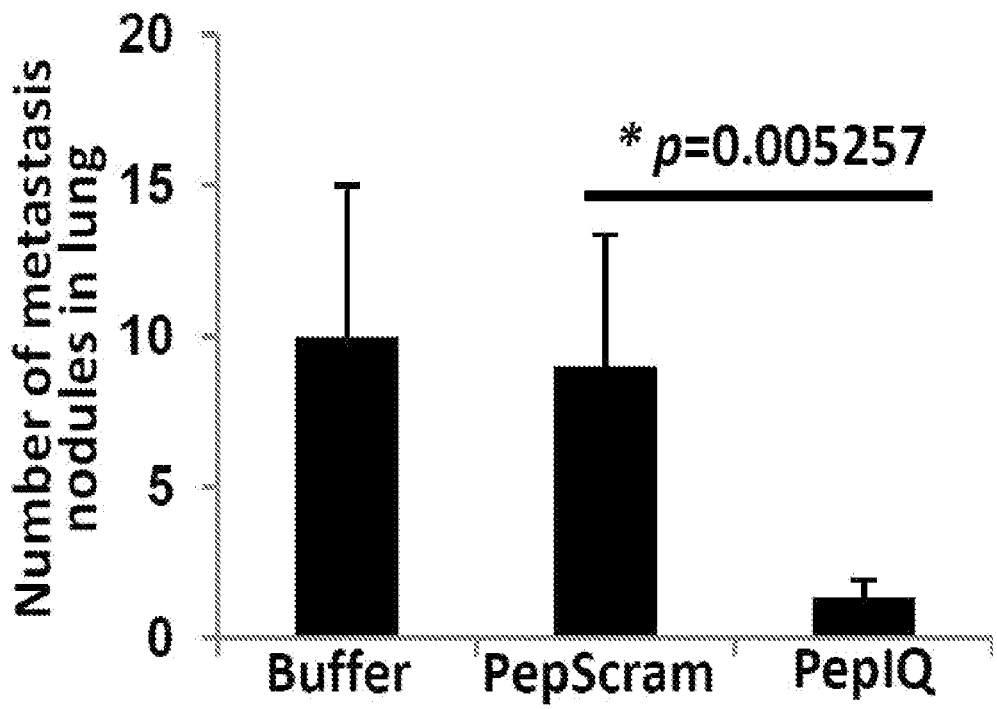
FIGS. 5B and 5C are bar graphs showing number (FIG. 5B) and mean volume (FIG. 5C) of metastasis nodules in the lung of 4T1 tumor bearing mice that were treated with buffer (column 1), PepScram (column 2), or PepIQ (column 3).
Figure 5C:
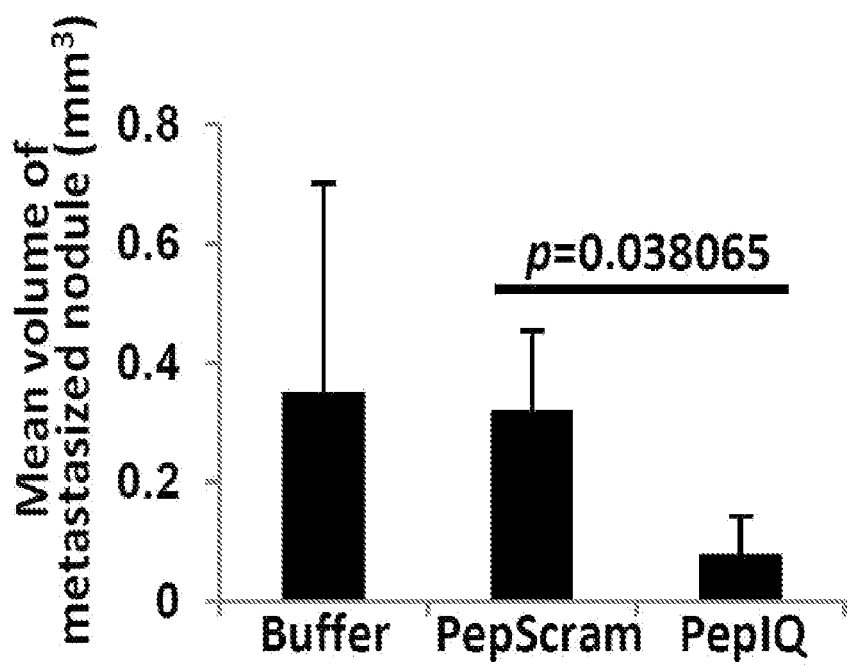
Figure 5D:
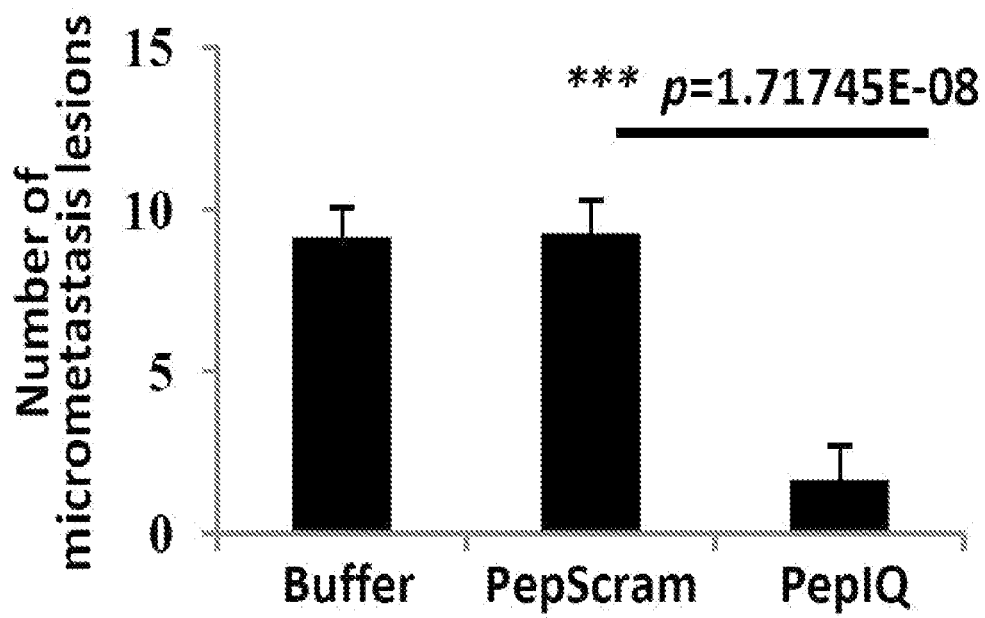
FIG. 5D is a bar graph showing the numbers of micrometastasis lesions in liver tissue sections from 4T1 tumor bearing mice that were treated with buffer (column 1), PepScram (column 2), or PepIQ (column 3). The numbers of micrometastasis lesion were counted by randomly selected 4 fields from randomly selected three tissue sections of each liver. p values were calculated by the pair-wise student t-tests.

The PepIQ was very effective in inhibiting cancer metastasis with xenograft model of SW620 cells, indicating a potential application for metastasis intervention using the peptide or its derivatives. Thus, the effects of the peptide on metastasis in another cancer model was tested. Mouse breast cancer 4T1 cells were implanted into mammary gland of Balb/c mouse. Four days post-tumor implantation, the mice were treated by the PepIQ, the control peptide (PepScram), and buffer by 2 mg/kg daily dose for 14 days via i.p. injection. The mice were sacrificed at 26 days after tumor implantation. The primary tumors and major metastasis organs, lungs and liver, were collected and examined. It was evident that the peptide treatments did not lead to any significant change in primary tumor growth (FIG. 5A, tumor in one mouse in the PepIQ treated group did not grow). The strong metastasis to lung with multiple metastasis sites was observed in the buffer and the PepScram treatment groups, while only 3 out of 4 mice had the cancer metastasis in the lung in the PepIQ treated group (one mouse was completely metastasis free in lung). The numbers of visible metastatic nodules in lung in the PepIQ treated group were much less and the nodules were much smaller than those in the PepScram and buffer treated groups (FIGS. 5B-5D). No visible metastasis nodules were observed in livers of all mice. However, histology analyses revealed micrometastasis lesions in the livers (FIG. 5D). Quantification of the micrometastasis lesions in randomly selected 4 fields from randomly selected three tissue sections of liver from each mouse revealed that the average numbers of micrometastasis lesions were substantially less in the PepIQ treated group compared to those of buffer and PepScram treated groups (FIG. 5D). No micrometatstasis lesion was seen in the liver tissue sections from two out of four mice in the PepIQ treated group. The size of micrometastasis lesions in the PepIQ treated group was also substantially smaller than that of control groups (FIG. 5D). To test whether the PepIQ also affected the cell migration of 4T1 cells, cell migration assays were conducted. Both Boyden chamber and scratch-wound assays indicated that the cell migration was dramatically reduced upon the PepIQ treatment (FIG. 10).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting metastasis of a cancer in a subject, comprising administering to a subject in need thereof a composition comprising an agent that selectively inhibits the binding of p68 RNA helicase having a IQ motif to calmodulin (CaM) in cancer cells, wherein the agent is a peptide having the IQ motif and selectively binds to the calmodulin in a p68-binding region of the calmodulin.

2. A method for treating an inflammatory disease in a subject, comprising administering to a subject in need thereof a composition comprising an agent that selectively inhibits the binding of p68 RNA helicase to calmodulin (CaM), wherein the agent is a peptide having an IQ motif and selectively binds to the calmodulin in a p68-binding region of the calmodulin.

3. The method of claim 1, wherein the peptide comprises the amino acid sequence FVSAGIQTSFRTGNPTG (SEQ ID NO:7).

4. The method of claim 1, wherein the peptide comprises the amino acid sequence FVSAGIQTSFRTGNPTGAYG (SEQ ID NO:4).

5. The method of claim 3, wherein the peptide further comprises a cell penetrating peptide sequence.

6. The method of claim 3, wherein the peptide is 6 to 30 amino acids in length.

7. An isolated peptide comprising the IQ motif of human p68 that binds human CaM, and a cell penetrating peptide sequence.

* * * * *